(12) United States Patent
Schlievert

(10) Patent No.: US 11,786,454 B2
(45) Date of Patent: Oct. 17, 2023

(54) COMPOSITIONS FOR TOPICAL TREATMENT OF MICROBIAL INFECTIONS

(71) Applicant: Hennepin Life Sciences, Plymouth, MN (US)

(72) Inventor: Patrick M. Schlievert, Iowa City, IA (US)

(73) Assignee: Hennepin Life Sciences, LLC, Plymouth, MN (US)

( * ) Notice: Subject to any disclaimer, the term of this patent is extended or adjusted under 35 U.S.C. 154(b) by 0 days.

(21) Appl. No.: 15/056,239

(22) Filed: Feb. 29, 2016

(65) Prior Publication Data
US 2016/0175244 A1    Jun. 23, 2016

Related U.S. Application Data

(62) Division of application No. 13/866,722, filed on Apr. 19, 2013, now Pat. No. 9,724,295.

(60) Provisional application No. 61/636,203, filed on Apr. 20, 2012, provisional application No. 61/650,755, filed on May 23, 2012.

(51) Int. Cl.
| | |
|---|---|
| *A61K 9/00* | (2006.01) |
| *A61K 31/23* | (2006.01) |
| *A61K 45/06* | (2006.01) |
| *A61K 9/06* | (2006.01) |
| *A61K 47/38* | (2006.01) |
| *A61K 31/04* | (2006.01) |
| *A61K 31/195* | (2006.01) |
| *A61K 47/10* | (2017.01) |
| *A61K 47/14* | (2017.01) |
| *A61K 47/44* | (2017.01) |

(52) U.S. Cl.
CPC ............. *A61K 9/0014* (2013.01); *A61K 9/06* (2013.01); *A61K 31/04* (2013.01); *A61K 31/195* (2013.01); *A61K 31/23* (2013.01); *A61K 45/06* (2013.01); *A61K 47/10* (2013.01); *A61K 47/14* (2013.01); *A61K 47/38* (2013.01); *A61K 47/44* (2013.01); *Y02A 50/30* (2018.01)

(58) Field of Classification Search
CPC ...... A61K 31/23; A61K 31/04; A61K 31/195; A61K 45/06; A61K 47/10; A61K 47/14; A61K 47/38; A61K 47/44; A61K 9/0014; A61K 9/06; A61P 17/00; A61P 31/00; A61P 31/04; A61P 31/10; A61P 31/12; A61P 31/16; A61P 31/18; A61P 31/22
See application file for complete search history.

(56) References Cited

U.S. PATENT DOCUMENTS

| | | |
|---|---|---|
| 4,746,515 A | 5/1988 | Cheng et al. |
| 5,208,257 A | 5/1993 | Kabara |
| 5,256,405 A | 10/1993 | Chappell et al. |
| 5,569,461 A | 10/1996 | Andrews |
| 5,906,814 A | 5/1999 | Epstein |
| 9,724,295 B2 | 8/2017 | Schlievert |
| 2002/0031556 A1 | 3/2002 | Lindahl |
| 2003/0003107 A1 | 1/2003 | Farmer |
| 2005/0058673 A1 | 3/2005 | Scholz |
| 2006/0029558 A1 | 2/2006 | Schlievert et al. |
| 2007/0276049 A1 | 11/2007 | Schlievert et al. |
| 2010/0130951 A1 | 5/2010 | Pierson |
| 2013/0281532 A1 | 10/2013 | Schlievert |
| 2018/0092835 A1 | 4/2018 | Schlievert |

FOREIGN PATENT DOCUMENTS

| | | |
|---|---|---|
| WO | 2005/023233 A2 | 3/2005 |
| WO | 2011035158 A2 | 3/2011 |
| WO | WO PCT/US15/014875 | 8/2015 |

OTHER PUBLICATIONS

"Preservation of Products with Surfactants" in: Kabara and Orth: "Preservative-free and self-preserving cosmetics and drugs—Principles and Practice", 1997, Marcel Dekker.
Loo Chew Hung; Rosnah Ismail et al : "Testing of glyceryl monoesters for their anti-microbial susceptibility and their influence in emulsions", Journal of Oil Palm Research, vol. 22, Dec. 2010.
A.O. Gill et al: "Evaulation of Antilisterial Action of Cilantro Oil on Vacuum Packed Ham", International Journal of Food Microbiology, vol. 73, No. 1, Feb. 25, 2002.
Kristmundsdottir T et al: Development and evaluation of microbial hydrogels containing monoglyceride as the active ingredient, Journal of Pharmaceutical Sciences, American Pharmaceutical Association, Washington, US, vol. 88, No. 10, Oct. 1, 1999.
Hegde, B. M.: "Coconut Oil—Ideal Fat Next Only to Mother's Milk (scanning coconut's horoscope)", Journal, Indian Academy of Clinical Medicine, vol. 7, No. 1, 2006.
Fu, X. et al. : "Physiochemical characterization and evaluation of a microemulsion system for antimicrobial activity of glycerol monolaurate", International Journal of Pharmaceutics, vol. 321, No. 1, 2006.
Schlievert, P.M. et al.: "Glycerol monolaurate does not alter rhesus macaque (*Macaca mulatta*) vaginal Lactobacilli and is safe for chronic use", Antimicrobial Agents and Chemotherapy, vol. 52, No. 12, 2008.
Schlievert, P.M. et al.: "Glycerol monolaurate antibacterial activity in broth and biofilm cultures", PLOS ONE, vol. 7, No. 7 Jul. 11, 2012.
Mueller et al., "Non-Aqueous Glycerol Monolaurate Gel Exhibits Antibacterial and Anit-Biofilm Activity against Gram-Positive and Gram-Negative Pathogens," PLOS One, DOI: 10.1371/jorunal.pone.0120280, Mar. 23, 2015, 12 pages.
Hasse et al., "Glycerol Monolaurate Microbicide Protection against Repeat High-Dose SIV Vaginal Challenge," PLOS One, DOI: 10.1371/jorunal.pone.0129465, Jun. 9, 2015, 12 pages.

(Continued)

*Primary Examiner* — Kara R Mcmillian
(74) *Attorney, Agent, or Firm* — Mintz Levin Cohn Ferris Glovsky and Popeo, P.C.

(57) ABSTRACT

The present invention provides compositions and methods for topical treatment of infections. The compositions comprise glycerol monolaurate or a derivative thereof, and are administered topically, for example, to treat viral, fungal or bacterial infections.

10 Claims, 25 Drawing Sheets

(56) References Cited

OTHER PUBLICATIONS

Kirtane et al., "Evaluation of Vaginal Drug Levels and Safety of a Locally Administered Glycerol Monolaurate Cream in Rhesus Macaques," downloaded from https://www.ncbi.nlm.nih.gov/pubmed/28389267, printed May 8, 2018, Abstract only, 1 page.

U.S. Appl. No. 15/967,844, titled "Topical Composition Comprising Glycerol Monolaurate", filed May 1, 2018.

Strandberg et al., "Glycerol Monolaurate Inhibits Candida and Gardnerella vaginalis In Vitro and In Vivo but Not Lactobacillus" Antimicrobial Agents and Chemotherapy, Feb. 2010, p. 597-601.

Andrei et al. (Oct. 20, 2011) "Topical Tenofovir, a Microbicide Effective Against HIV, Inhibits Herpes Simplex Virus-2 Replication", Cell Host & Microbe, 10:379-389.

Elci et al. (2003) "Effect of Glycerol Monolaurate and Sodium Benzoate at Different Concentrations, Temperatures and pH on the Growth of Listeria Monocytogenes", Biotechnology & Biotechnological Equipment, 17(2):123-127.

Oh et al. (Jun. 1992) "Effect of pH on the Minimum Inhibitory Concentration of Monolaurin Against Listeria Monocytogene", Journal of Food Protection, 55(6):449-450.

Thormar et al. (Jun. 6, 1994) "Inactivation of Visna Virus and Other Enveloped Viruses by Free Fatty Acids and Monoglycerides", Annals of the New York Academy of Sciences, 724:465-471.

Figure 13
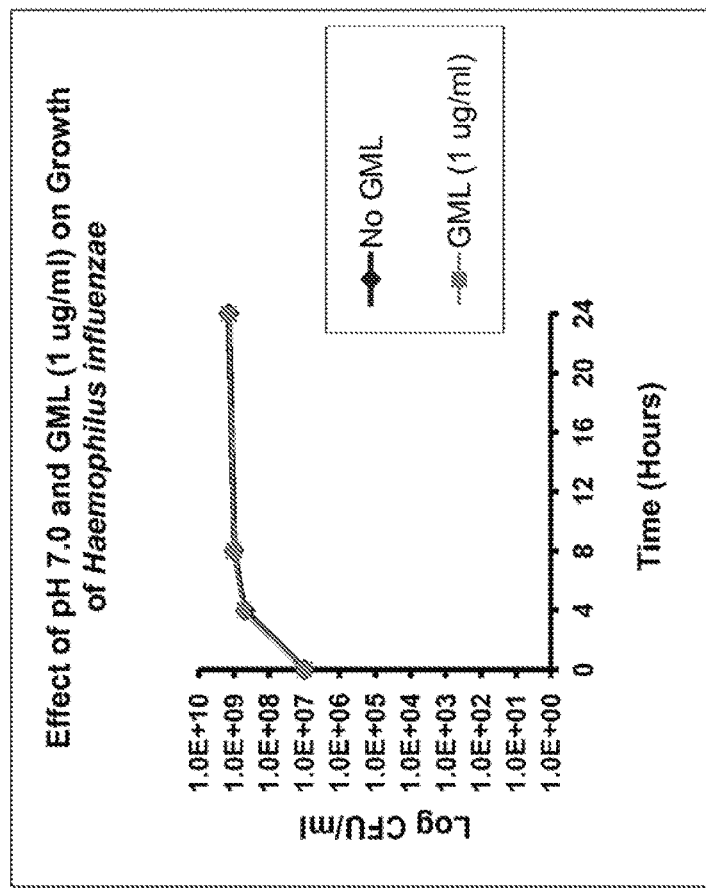
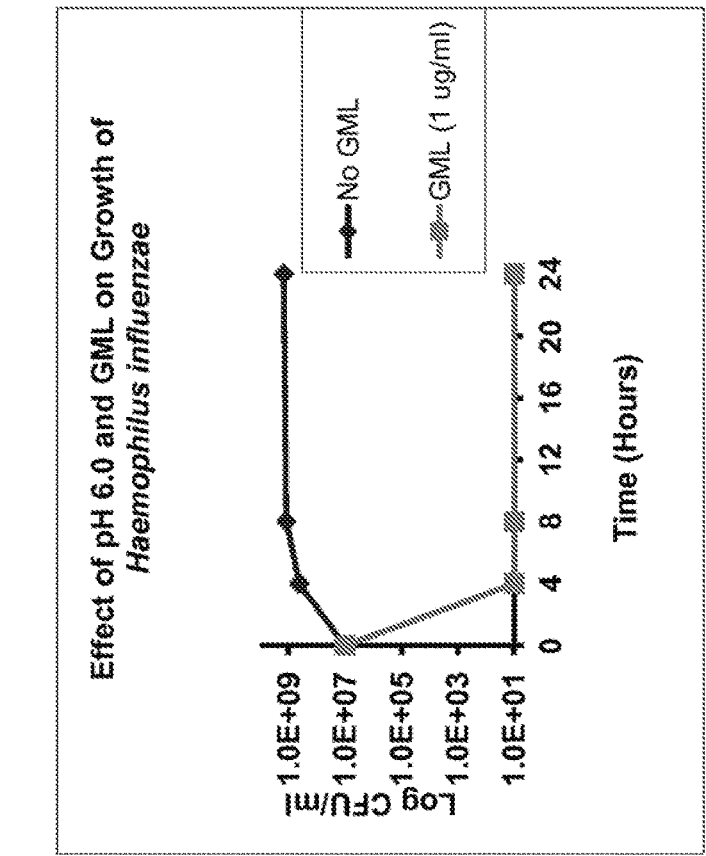

Figure 20

Figure 25
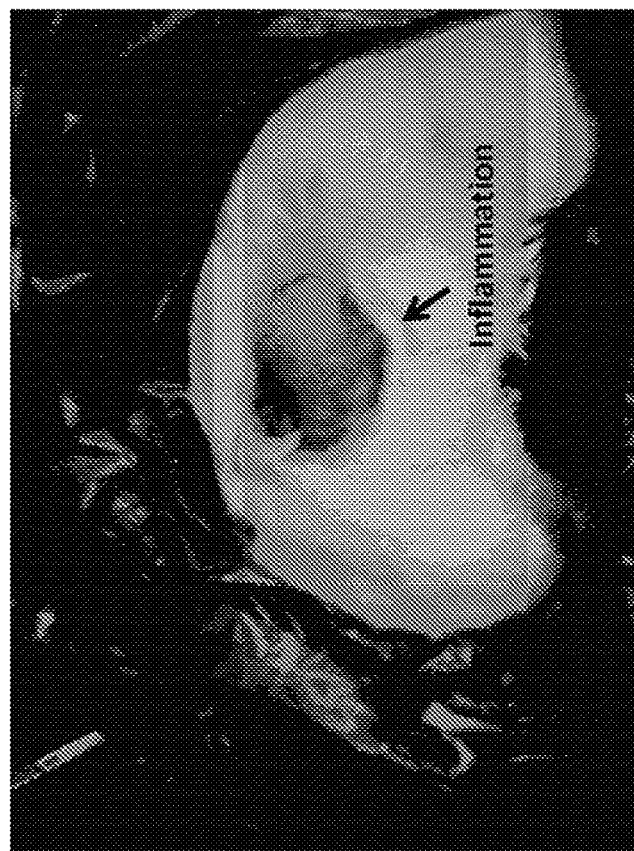
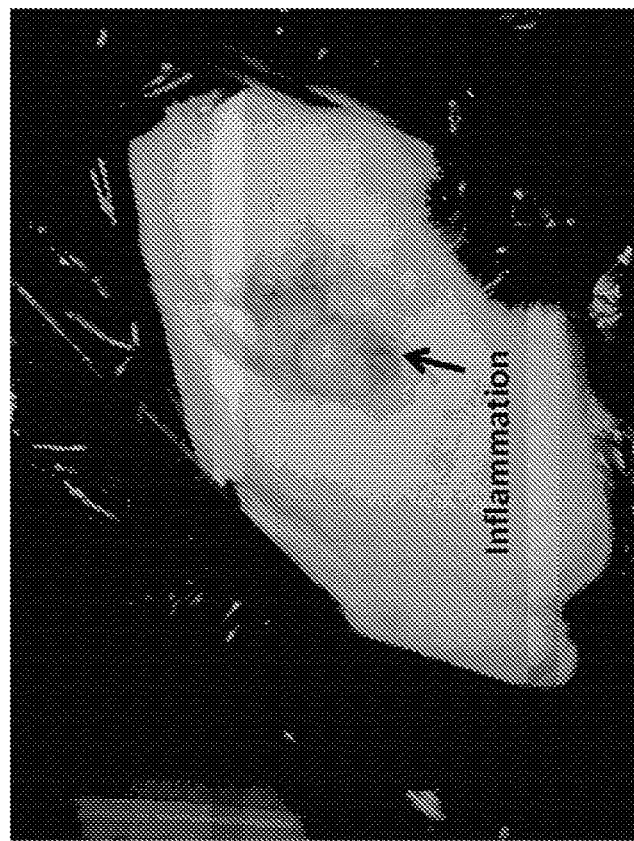

COMPOSITIONS FOR TOPICAL TREATMENT OF MICROBIAL INFECTIONS

CROSS REFERENCE TO RELATED APPLICATIONS

This application is a division of application Ser. No. 13/866,722 filed Apr. 19, 2013, now U.S. Pat. No. 9,724,295, which claims the benefit of U.S. provisional application No. 61/636,203, filed Apr. 20, 2012, and U.S. provisional application No. 61/650,755, filed May 23, 2012, each of which is incorporated by reference in their entireties.

BACKGROUND OF THE INVENTION

Some bacterial pathogens initiate human illnesses from intact or damaged mucosal or skin surfaces. Many of these pathogens are acquired from other persons or animals, from endogenous sources, or from a myriad of environmental sources. Once in humans, pathogens colonize surfaces primarily as biofilms of organisms, defined as thin-films of organisms attached to host tissues, medical devices, and other bacteria through complex networks of polysaccharides, proteins, and nucleic acids. These bacteria may also exist as planktonic (broth) cultures in some host tissue environments, such as the bloodstream and mucosal secretions. Similarly, these potential pathogens may exist as either biofilms or planktonic cultures in a myriad of non-living environments.

Glycerol monolaurate (GML) is a naturally occurring glycerol-based compound that has previously been shown to have anti-microbial, anti-viral, and anti-inflammatory properties. The present invention provides GML compositions and methods for the treatment of various microbial infections and illnesses resulting from one or more microbial infections.

SUMMARY OF THE INVENTION

Simple, inexpensive, and well tolerated methods and compositions are needed for applying anti-microbial compounds such as GML at effective levels to skin and mucosal surfaces of humans and other vertebrates. The present invention addresses this and other needs.

In one aspect, the present invention is directed to a composition comprising glycerol monolaurate (GML) or a derivative thereof, and a vegetable oil. In one embodiment, the vegetable oil is palm, olive, corn, canola, coconut, soybean, or wheat, or a combination thereof. In a further embodiment, the vegetable oil is present in the composition at about 10% to about 99%, about 20% to about 90%, about 30% to about 80%, or about 40% to about 70%. In one embodiment, the composition comprising GML or a derivative thereof and a vegetable oil further comprises a pharmaceutically acceptable topical carrier, for example, petroleum jelly. In one embodiment, GML or a derivative thereof is present in the composition at a concentration from about 10 µg/mL to about 100 mg/mL, from about 50 µg/mL to about 50 mg/mL, from about 100 µg/mL to about 10 mg/mL, or from about 500 µg/mL to about 5 mg/mL. In another embodiment, the composition comprising GML or a derivative thereof and a vegetable oil further comprises a cellulose derivative, for example either hydroxypropyl cellulose or hydroxyethyl cellulose, or a combination thereof. In a further embodiment, the cellulose derivative is present in the composition up to 1.25% w/w.

In another aspect, the present invention is directed to a composition comprising GML or a derivative thereof, and a non-aqueous gel. In one embodiment, the composition comprising GML or a derivative thereof and a non-aqueous gel has a pH of about 4.0 to about 4.5. In one embodiment, the non-aqueous gel comprises polyethylene glycol, hydroxypropyl cellulose, hydroxyethyl cellulose, or a combination thereof. In a further embodiment, the polyethylene glycol is present at about 25% w/w in the composition. In one embodiment, hydroxypropyl cellulose and hydroxyethyl cellulose are both present in the composition, each at a concentration of about 1.25% w/w.

In one embodiment, the GML composition comprising a non-aqueous gel comprises polyethylene glycol with a molecular weight range of about 300 to about 4000. In a further embodiment, the polyethylene glycol has a molecular weight of about 400 or about 1000.

In one embodiment, the GML composition comprising a non-aqueous gel further comprises a topical carrier, e.g., petroleum jelly. In a further embodiment, the composition comprises a vegetable oil.

In one embodiment, the compositions described herein comprise GML or a derivative thereof at a concentration of about 0.001% (w/v) to about 10% (w/v) of the total composition. In a further embodiment, GML or a derivative thereof is present at about 0.005% (w/v) to about 5% (w/v) of the composition. In a further embodiment, GML or a derivative thereof is present at about 0.01 to about 1%. In a still further embodiment, GML or a derivative thereof is present at about 0.1% (w/v) to about 0.5% (w/v) of the composition.

In one embodiment, GML or a derivative thereof is present in the composition at a concentration of about 10 µg/mL to about 100 mg/mL. In a further embodiment, GML or a derivative thereof comprises about 50 µg/mL to about 50 mg/mL of the composition. In a further embodiment, GML or a derivative thereof comprises about 100 µg/mL to about 10 mg/mL. In a still further embodiment, GML or a derivative thereof comprises about 500 µg/mL to about 5 mg/mL.

In one embodiment, the GML composition provided herein comprises propylene glycol at a concentration of about 65% (w/w) to about 80% (w/w). In another embodiment, polyethylene glycol is present in the composition at a concentration of about 20% (w/w) to about 35% (w/w). In one embodiment, both propylene glycol and polyethylene glycol are present in the topical composition.

In one embodiment, the composition comprises a cellulose derivative. In a further embodiment, the composition comprises hydroxypropyl cellulose or hydroxyethyl cellulose. In a yet further embodiment, the cellulose is present at a concentration of about 0.1% (w/w) to about 5.0% (w/w).

In one embodiment, the GML composition comprises an aqueous solvent. In a further embodiment, the aqueous solvent is water, saline, media, or a combination thereof.

In one embodiment, the pharmaceutically acceptable topical carrier is petroleum jelly.

In one embodiment, the pH of the GML composition provided herein is from about 4.0 to about 5.5.

In some embodiments, the composition provided herein comprises one or more accelerants. In a further embodiment, the accelerant is an organic acid, a chelator, an anti-bacterial agent, an anti-fungal agent, an anti-viral agent, or a combination thereof. In a further embodiment, the accelerant is a chelator. In even a further embodiment, the accelerant is EDTA.

In another aspect, the GML composition provided herein has anti-microbial, anti-viral, and/or anti-inflammatory activity. For example, in one embodiment, the composition provided herein is applied topically to humans and other vertebrates, for example for treatment of a bacterial, fungal, or viral infection such as *Gardnerella vaginalis* or *Candida albicans*.

Accordingly, in one embodiment, the present invention provides methods for treating a microbial infection in a subject in need thereof. In one embodiment, the method comprises topically administering to the subject in need thereof, an effective amount of a GML composition provided herein. In one embodiment, the composition comprises GML or a derivative thereof, a vegetable oil, and a pharmaceutically acceptable topical carrier. In another embodiment, the composition comprises GML or a derivative thereof, a non-aqueous gel, and a pharmaceutically acceptable topical carrier. In a further embodiment, the composition comprises GML or a derivative thereof, a vegetable oil, a non-aqueous gel, and a pharmaceutically acceptable topical carrier.

In one embodiment, the compositions disclosed herein are applied topically with the use of a sponge, wipe, or swab.

In one embodiment, the subject has a bacterial infection. In a further embodiment, the bacterial infection is *Staphylococcus* (such as *Staphylococcus aureus*); *Streptococcus* (such as *Streptococcus pneumoniae* or *Streptococcus agalactiae*); *Escherichia* (such as *Escherichia coli*); *Gardnerella* (such as *Gardnerella vaginalis*); *Clostridium* (such as *Clostridium peifringens*); *Mycobacterium* (such as *Mycobacterium tuberculosis* or *Mycobacterium phlei*); or *Chlamydia* (such as *Chlamydia trachomatis*).

In another embodiment, the subject treated with one of the GML compositions provided herein has a fungal infection. In a further embodiment, the fungal infection is *Candida* (such as *Candida albicans*), *Microsporum* species, *Trichophyton* species, *Penicillium* species, or *Aspergillus* species.

In another embodiment, the method of the invention involves administering a second active agent selected from the group consisting of anti-fungal agents, anti-viral agents, and antibiotics.

BRIEF DESCRIPTION OF THE FIGURES

FIG. 13 is a set of graphs showing CFU/mL from *H. influenzae* cultures grown at the indicated pH, in the presence of the 1 µg/mL GML.

FIG. 20 is a graph showing superantigen production from S. aureus (TSST-1) or S. pyogenes (SPE A) in the presence of GML or lauric acid.

FIG. 25 shows the inflammation present at surgical incision sites of New Zealand white rabbits treated with S. aureus MN8 and then GML gel (left) or PBS (right) for 24 hours. Inflammation is apparent as dark grey coloring of the surgical site, as indicated by the arrows.

DETAILED DESCRIPTION OF THE INVENTION

Figure 1:
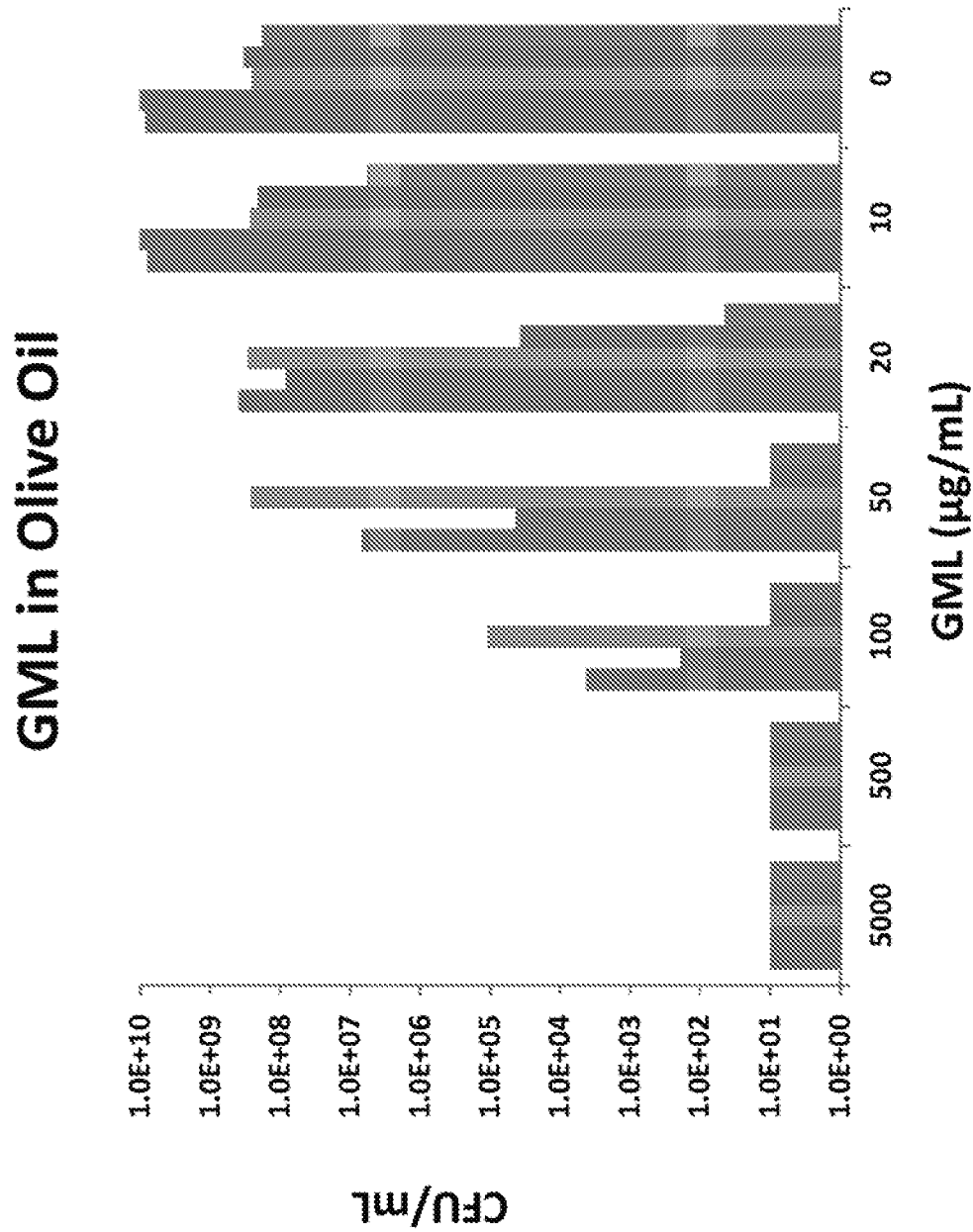
FIG. 1 is a graph showing the effect of various concentrations of GML in olive oil on the growth of several microorganisms (measured as CFU/mL). Bars represent the following microorganisms, from left: *Staphylococcus aureus* MNPE (methicillin sensitive strain), *S. aureus* MW2 (methicillin resistant strain), *Candida albicans*, *Streptococcus agalactiae*, and *Gardnerella vaginalis*.

The present invention provides topical GML compositions and methods of treatment with the compositions, e.g., by topical administration. The compositions and methods provided herein, in one embodiment, are used for treating infections topically, for example, by facilitating delivery of effective amounts of GML or a derivative thereof to a skin or mucosal surface of a subject, e.g., a human. Without wishing to be bound by theory, it is believed that the compositions of the invention result in greater patient compliance for topical self-administration due to the less irritating nature of the composition, relative to previously employed topical formulations of anti-microbial and anti-viral compounds.

As used herein, the term "antimicrobial" means effective in preventing, inhibiting, or arresting the growth or pathogenic effects of a microorganism. "Microorganism" is used herein to mean any bacteria, virus, or fungus. In one embodiment, the formulations of the invention are used to prevent, inhibit, or arrest the growth of one or more of the following microorganisms: Staphylococcus aureus, Streptococcus (e.g., S. pyogenes, S. agalacticae or S, or S. pneumoniae) Haemophilus influenzae, Pseudomonas aeruginosa, Gardnerella vaginalis, Enterobacteriacae (e.g., Escherichia coli), Clostridium peifringens, Chlamydia trachomatis, Candida albicans, Human Immunodeficiency Virus (HIV), or Herpes Simplex Virus (HSV).

"Anti-bacterial" or "anti-fungal," as used herein, refer to inhibition or arrest of the growth of a bacterium or fungus, a reduction in the severity of or likelihood of developing a bacterial or fungal disease, inducing death of the bacterium or fungus or reduction or inhibition of the pathogenic effects of the respective bacterium or fungus. "Bactericidal" is used interchangeably with "anti-bacterial."

"Anti-viral," as used herein, refers to inhibition of viral infection or virus replication, a reduction in the likelihood that a subject exposed to a virus will contract the viral disease, or a reduction in the severity of the viral disease.

The term "effective amount," as used herein, refers to an amount that is sufficient to effect a beneficial or desired antimicrobial activity, including, without limitation, killing the microorganism or inhibiting microbial infection, growth or toxicity. An effective amount of GML is about 10 µg/mL, about 100 µg/mL, about 1 mg/mL, about 10 mg/mL, about 50 mg/mL, or about 100 mg/mL.

The terms "treat," "treatment," and "treating" refer to an approach for obtaining beneficial or desired results, for example, clinical results. For the purposes of this invention, beneficial or desired results may include inhibiting or suppressing the growth of a microorganism or killing a microorganism; inhibiting one or more processes through which a microorganism infects a cell or subject; inhibiting or ameliorating the disease or condition caused by a microbial infection; or a combination thereof. The terms "treat," "treatment," or "treating" also refer to prophylaxis of infection. In some embodiments, the formulations of the invention are used to treat urinary tract infections, vaginal microbial infections, infections of the oral cavities such as those causing gum disease, post-surgical infections including respiratory tract infections, wound or surgical incision site infections, or infections characterized by the production of toxins, including Toxic Shock Syndrome.

"Prophylaxis," as used herein, can mean complete prevention of an infection or disease, or prevention of the development of symptoms of that infection or disease; a delay in the onset of an infection or disease or its symptoms; or a decrease in the severity of a subsequently developed infection or disease or its symptoms.

As used herein, the term "subject" includes humans and other animals. The subject, in one embodiment, is a human.

"Topical," as used herein, refers to the application of the composition to any skin or mucosal surface. "Skin surface" refers to the protective outer covering of the body of a vertebrate, generally comprising a layer of epidermal cells and a layer of dermal cells. A "mucosal surface," as used herein, refers to a tissue lining of an organ or body cavity that secretes mucous, including but not limited to oral, vaginal, rectal, gastrointestinal, and nasal surfaces. In one embodiment, the formulations of the invention are administered topically to the teeth and gum, skin, nasal, or vaginal areas.

The term "pharmaceutically acceptable topical carrier," as used herein, refers to a material, diluent, or vehicle that can be applied to skin or mucosal surfaces without undue toxicity, irritation, or allergic reaction.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

As used herein, the term "vegetable oil" means a substance extracted from a plant or seed that exists in liquid form at room temperature. Suitable vegetable oils include, without limitation, palm, olive, corn, canola, coconut, soybean, wheat germ, jojoba, sunflower, sesame, peanut, cottonseed, safflower, soybean, rapeseed, almond, beech nut, cashew, hazelnut, macadamia, mongongo nut, pecan, pine nut, pistachio, walnut, grapefruit seed, lemon, orange, bitter gourd, bottle gourd, buffalo gourd, butternut squash seed, egusi seed, pumpkin seed, watermelon seed, acai, black seed, blackcurrant seed, borange seed, evening primrose, flaxseed, eucalyptus, amaranth, apricot, apple seed, argan, avocado, babassu, coriander seed, grape seed, mustard, poppyseed, rice bran, castor, or mixtures thereof. Mixtures can be, by way of example and without limitation, a combination of olive oil and soybean oil, a combination of coconut oil and wheat germ oil, or a combination of jojoba oil, palm oil, and castor oil. Mixtures of vegetable oils can be binary, ternary, quaternary, or higher mixtures.

The term "accelerant," as used herein, refers to a compound, substance, liquid, powder, or mixture that, when added to the composition, has the effect of enhancing or contributing to the antimicrobial properties of the composition. Accelerants may be an organic acid including, without limitation, lactic acid, ascorbic acid, citric acid, formic acid, benzoic acid, and oxalic acid. The accelerant, in another embodiment, is a chelator, and in one embodiment, is selected from ethylenediaminetetraacetic acid (EDTA), dimercaprol, dimercaptosuccinic acid (DMSA), 2,3-dimercapto-1-propanesulfonic acid (DMPS), alpha lipoic acid (ALA), or combinations thereof. In another embodiment, the accelerant is selected from an antibiotic agent, anti-fungal agent, anti-viral agent, or combination thereof. Antibiotics for use with the invention, for example, include aminoglycosides, carbacephems, cephalosporins, glycopeptides, lincosamides, lipopetides, macrolides, monobactams, nitrofurans, penicillins, polypetides, quinolones, sulfuramides, and tetracyclines. Anti-fungal agents include, without limitation, those of the azole class, polyene class, or echinocanins class, nucleoside analogues, allylamines, griseofulvin, tolnaftate, or selenium compounds. Anti-viral agents include, for example and without limitation, acyclovir, ganciclovir, valganciclovir, abacavir, enofovir, lamivudine, emtricitabine, zidovudine, tenofovir, efavirenz, raltegravir, enfuvirdide, maraviroc, ribavirin, amantadine, rimantadine, interferon, oseltamivir, and zanamivir.

As used herein, the term "cellulose derivative" refers to any a cellulose-based compound and may include, for example, hydroxyethyl cellulose, hydroxypropyl cellulose, methylcellulose, ethylcellulose, hydroxypropyl methyl cellulose, or cellulose acetate.

The term "biofilm," as used herein, means an aggregate of microorganisms, usually bacterial, adhered to one another and growing on a surface. The microbial cells in the biofilm typically produce an extracellular matrix known as an extracellular polymeric substance. Often, this matrix and the density of the aggregate itself significantly increase the antibiotic resistance of the bacteria in the biofilm. Biofilms can be involved in UTis, ear infections, and dental diseases such as gingivitis, and can also form on the surface of implanted devices including prostheses, catheters, or heart valves.

In one aspect, the present invention provides a topical composition comprising glycerol monolaurate (GML) or a derivative thereof. In a further embodiment, the composition comprises a vegetable oil or a non-aqueous gel, or a combination thereof. The non-aqueous gel, in one embodiment, comprises a cellulose derivative. The topical composition provided herein, in one embodiment, comprises a pharmaceutically acceptable topical carrier.

In one embodiment, the composition provided herein comprises the monoglyceride GML. GML is a fatty acid ester of glycerol, derivative of lauric acid, with the chemical formula C15H3004. GML is also known in the art as glyceryl laurate or monolaurin. GML is found naturally in breast milk and some plants, and is used as a food and cosmetic additive. GML and other glycerides are listed in the Generally Recognized as Safe Substances database by the US Food and Drug Administration. GML and related compounds have been previously disclosed in U.S. patent application Ser. No. 10/579,108 (filed Nov. 10, 2004) and Ser. No. 11/195,239 (filed Aug. 2, 2005), the disclosures of each of which are herein incorporated by reference for all purposes.

GML can be synthesized in multiple forms including both R and S optical isomers, as well as forms with lauric acid in the 1/3-position and in the 2-position. The composition provided herein, in one embodiment, comprises the R isomer of GML. In another embodiment, the composition provided herein comprises the S isomer of GML. In yet another embodiment, a racemic mixture of isomers is provided in the composition.

Similarly, the topical composition may comprise GML with lauric acid at the 1/3 position, GML with lauric acid at the 2-position, or a combination thereof. R and S isomers of each form, and racemic mixtures thereof, are amenable for use with the present invention.

The chemical structure of GML with lauric acid in the 1/3-position is

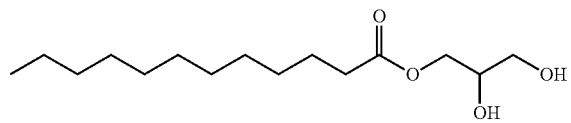 [SMILES: CCCCCCCCCCCC(=O)OCC(O)CO]

Glycerol monolaurate (GML) 1/3-position

The chemical structure of GML with lauric acid in the 2-position is:

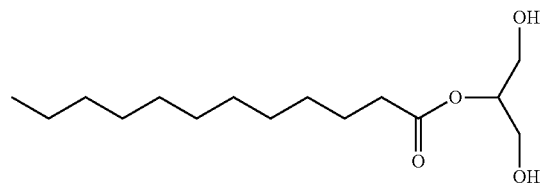 [SMILES: CCCCCCCCCCCC(=O)OC(CO)CO]

Glycerol monolaurate (GML) 2-position

In another embodiment, the topical composition comprises a GML derivative, for example a compound selected from one of Formulae I-VI. Examples of such compounds include, by way of example and without limitation, glycerol monocaprylate, glycerol monocaprate, glycerol monomyristate, glycerol monopalmitate, and dodecyl glycerol.

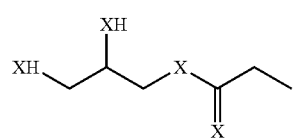

Formula I

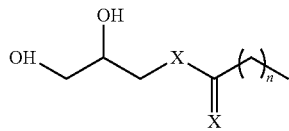

Formula II

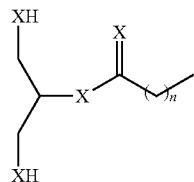

Formula III

-continued

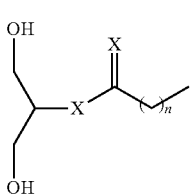

Formula IV wherein each occurrence of X is independently —O— or —S—; and n is an integer from 5 to 20 (inclusive).

In another embodiment, the topical composition comprises at least one derivative of GML, and the at least one derivative is a compound of either Formula V or Formula VI. Examples of such compounds include, but are not limited to, glycerol dilaurate, glycerol dicaprylate, glycerol dimyristate, glycerol trilaurate, and glycerol tripalmitate.

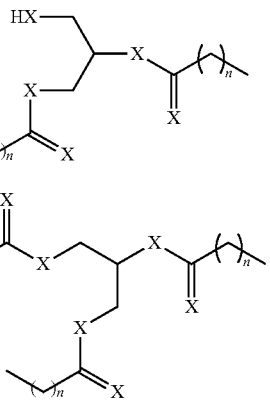

Formula V

Formula VI wherein each occurrence of X is independently —O— or —S—; and
each occurrence of n is independently an integer from 5 to 20 (inclusive).

In one embodiment, a compound of Formula I, II, III or IV is present in the topical composition of the invention, and at least one —X— is —S—. In one embodiment, one occurrence of —X— is —S— and the remaining occurrences of —X— are —O—.

In one embodiment, a compound of Formula V or VI is present in the topical composition of the invention, each occurrence of n is 10, and at least one —X— is —O—.

The topical composition provided herein, in one embodiment, comprises GML and a GML derivative. For example, in one embodiment, the topical composition provided herein comprises GML and a compound of Formula VI. In a further embodiment, each occurrence of n is 10 and at least one —X— is —O—.

In one embodiment, the topical composition comprises GML or a derivative thereof from about 0.001% (w/v) to about 10% (w/v) of the composition. In a further embodiment, GML or a derivative thereof comprises about 0.005% (w/v) to about 5% (w/v) of the composition. In a still further embodiment, GML or a derivative thereof comprises about 0.01%/(w/v) to about 1.0% (w/v) of the composition. In yet a further embodiment, GML or a derivative thereof comprises about 0.05% (w/v) to about 0.5% (w/v) of the composition.

In another embodiment, the topical composition comprises GML or derivative thereof at a concentration of about 10 μg/mL to about 100 mg/mL. In a further embodiment, the topical composition comprises GML or derivative thereof at a concentration of about 50 μg/mL to about 50 mg/mL. In a further embodiment, the topical composition comprises GML or derivative thereof at a concentration of about 100 μg/mL to about 10 mg/mL. In yet a further embodiment, the topical composition comprises GML or a derivative thereof at a concentration of about 500 μg/mL to about 5 mg/mL.

In one embodiment, the topical composition comprises GML or derivative thereof at a concentration of about 10 μg/mL, about 50 μg/mL, about 100 μg/mL, about 500 μg/mL, about 1 mg/mL, about 5 mg/mL, about 10 mg/mL, about 50 mg/mL, or about 100 mg/mL.

The amount of GML or derivative thereof in the composition can be tailored accordingly to the indication/disease being treated as well as the characteristics of the subject being treated. The amount of GML in the composition may vary depending on, for example, the nature of the infection or illness; the site of administration; the subject's medical history, subject weight, age, sex, and surface area being treated; and whether the subject is receiving any other medications.

As provided above, in one aspect, the present invention is directed to a topical composition comprising GML or a derivative thereof. In one embodiment, the topical composition comprises at least one glycol. For example, in one embodiment, the topical composition comprises propylene glycol, polyethylene glycol, or a combination thereof. In one embodiment, the polyethylene glycol has a molecular weight (MW) range from about 300 to about 10,000. In a further embodiment, the polyethylene glycol has a molecular weight of about 300 to about 1,000. In a still further embodiment, the polyethylene glycol has a molecular weight of about 400.

In one embodiment, polyethylene glycol is present in the topical composition. In a further embodiment, the polyethylene glycol has a MW of about 400, about 500 or about 1,000. In one embodiment, the polyethylene glycol is present in the topical composition at a concentration (w/w) of about 15% to about 50%, about 20% to about 40%, or about 25% to about 35%, for example, about 15%, about 20%, about 25%, about 30%, about 35%, about 40%, about 45%, or about 50%. In a further embodiment, both propylene glycol and polyethylene glycol are present in the topical composition. In a further embodiment, propylene glycol is present at a concentration of about 70% to about 80% and polyethylene glycol is present at a concentration of about 20% to about 30%. In even a further embodiment, the polyethylene glycol is polyethylene glycol 400.

In another embodiment, a topical composition comprising GML or a derivative thereof is provided. In a further embodiment, propylene glycol is present in the composition. In yet a further embodiment, propylene glycol is present in the composition at a concentration of about 60% to about 80%/a, for example, about 60%, about 65%, about 70%, about 71%, about 72%, about 73%, about 74%, about 75%, or about 80%.

In another embodiment, a topical composition comprising GML or a derivative thereof is provided. In one embodiment, the topical composition comprises at least one cellulose derivative. In a further embodiment, the composition comprises one cellulose derivative or two cellulose derivatives. In one embodiment, the cellulose derivative is hydroxypropyl cellulose. In another embodiment, the cellulose derivative is hydroxyethyl cellulose, carboxymethyl cellulose or hydroxymethyl cellulose. In yet another embodiment, the composition comprise a combination of hydroxyethyl cellulose and hydroxypropyl cellulose. In one embodiment, the cellulose derivative is present at a concentration of about 0.1% (w/w) to about 5.0% (w/w). In a further embodiment, multiple cellulose derivatives are present in the composition at the same concentration. In a further embodiment, two cellulose derivatives are present, and each is present at a concentration of about 1.25% (w/w). Cellulose derivatives include, for example, hydroxyethyl cellulose, hydroxypropyl cellulose, methylcellulose, ethylcellulose, hydroxypropyl methyl cellulose, or cellulose acetate.

In one embodiment, the topical composition provided herein comprises GML or a derivative thereof, at least one cellulose derivative, propylene glycol and polyethylene glycol.

In another embodiment, a topical composition comprising GML or a derivative thereof is provided. In a further embodiment, the composition comprises at least one vegetable oil, for example, at least one of the vegetable oils described above (e.g., palm oil, olive oil, corn oil). In one embodiment, the vegetable oil is present in the composition at a concentration of about 0.1% (w/w) to about 10% (w/w). In a further embodiment, the vegetable oil is present in the composition at a concentration of about 1% (w/w) to about 8% (w/w). In a further embodiment, the vegetable oil is present in the composition at a concentration of about 1% (w/w) to about 6% (w/w). In a further embodiment, the vegetable oil is present in the composition at a concentration of about 1% (w/w) to about 4% (w/w). In one embodiment, the vegetable oil is present in the composition at a concentration of about 0.1% (w/w), about 0.5% (w/w) about 1.0%0/(w/w), about 1.25% (w/w), about 1.5% (w/w), about 1.75% (w/w), or about 2.0% (w/w).

In one embodiment, the topical composition provided herein comprises a vegetable oil and at least one cellulose derivative. For example, in one embodiment, the topical composition comprises hydroxypropyl cellulose and a vegetable oil, or hydroxyethyl cellulose and a vegetable oil, or a combination of hydroxypropyl cellulose, hydroxyethyl cellulose, and a vegetable oil. In one embodiment, the cellulose derivative and the vegetable oil (e.g., palm, oil or corn oil), are each present at the same concentration (w/w). In a further embodiment, the cellulose derivative and the vegetable oil are each present in the composition at about 1% (w/w) to about 5% (w/w). In even a further embodiment, the cellulose derivative is a combination of hydroxypropyl cellulose and hydroxyethyl cellulose, and each is present in the composition at about 1.25% (w/w). In one embodiment, the composition comprises a vegetable oil and two cellulose derivatives. In a further embodiment, the two cellulose derivatives are hydroxypropyl cellulose and hydroxyethyl cellulose, and the total concentration of cellulose derivatives in the composition is about 1.25% (w/w). Cellulose derivatives include, for example, hydroxyethyl cellulose, hydroxypropyl cellulose, methylcellulose, ethylcellulose, hydroxypropyl methyl cellulose, or cellulose acetate.

In some embodiments, the topical composition provided herein comprises one or more accelerants. In a further embodiment, the accelerant is an organic acid, a chelator, an anti-bacterial agent, an anti-fungal agent, an anti-viral agent, or a combination thereof. In a further embodiment, the accelerant is a chelator. In even a further embodiment, the accelerant is EDTA.

The accelerant, in one embodiment, is EDTA. In a further embodiment, the GML composition provided herein comprises EDTA at a concentration of about 0.00005 M, about 0.0005 M, about 0.005 or about 0.05 M. In another embodiment, a chelator is present in the composition at a concentration of about 0.00005 M to about 0.05 M, about 0.0005 M to about 0.005 M, or about 0.005 to about 0.05 M.

In one embodiment, the topical composition comprises both a vegetable oil and an accelerant, for example palm oil and EDTA. In another embodiment, the accelerant is an organic acid and is present in the formulation with a vegetable oil. In one embodiment, the topical composition provided herein comprises an accelerant and a non-aqueous gel, for example a gel comprising a cellulose derivative. In another embodiment, the topical composition comprises GML or a derivative thereof, a vegetable oil, a non-aqueous gel (e.g., a gel comprising one or more cellulose derivatives) and an accelerant.

In one embodiment, the composition contains at least one pharmaceutically acceptable excipient. Pharmaceutically acceptable excipients are well known to those skilled in the art and may include buffers (e.g., phosphate buffer and citrate buffer), amino acids, alcohols, proteins such as serum albumin, parabens (e.g., methylparaben), or mannitol.

In one embodiment, the pH of the composition is from about 3.5 to about 7.0. In a further embodiment, the pH of the composition is from about 4.0 to about 6.0. In a still further embodiment, the pH of the composition is from about 4.0 to about 4.5.

In one embodiment, the composition provided herein comprises GML or a derivative thereof and a pharmaceutically acceptable topical carrier. In one embodiment, the pharmaceutically acceptable topical carrier is a mix of hydrocarbons such as, for example, paraffin wax or petroleum jelly. Petroleum jelly is any water-insoluble, hydrophobic, semi-solid mixture of hydrocarbons. The pharmaceutically acceptable topical carrier can be added to any of the formulations described herein.

In another embodiment, the composition comprises an aqueous solvent. Compositions comprising an aqueous solvent may or may not include a pharmaceutically acceptable topical carrier. In one embodiment, the aqueous solvent is present, and is water, saline, growth medium (e.g., microbial culture medium or cell culture medium), or a combination thereof. In a further embodiment, both an aqueous solvent and pharmaceutically acceptable topical carrier are present in the topical composition. In even a further embodiment, the topical composition comprises at least one cellulose derivative.

In one embodiment, the composition comprises bacterial culture media such as Todd Hewitt media as the aqueous solvent. In one embodiment, the aqueous solvent is present at a concentration of about 1% (w/w) to about 25% (w/w). In a further embodiment, the aqueous solvent is about 2% (w/w) to 5% (w/w) of the composition.

In one embodiment, the composition is a liquid solution. In another embodiment, the composition is a gel. In another embodiment, the composition is a solid, semi-solid, foam, wax, cream, or lotion.

In one embodiment, the composition comprises one of the formulations provided in Table 1. The vegetable oil, in one embodiment, is palm, olive or corn vegetable oil. It should be noted that Table 1 is merely exemplary of the composition components and concentrations that can be used with the present invention.

TABLE 1

Exemplary GML Formulations

| Formulation | Components | Concentration (if applicable) |
|---|---|---|
| 1 | GML | 0.001%-10% w/v (10 µg/mL-100 mg/mL) |
|  | Cellulose derivative 0.1% (w/w) to 5.0% (w/w) |  |
|  | Vegetable oil | up to 100% w/v |
| 2 | GML | 0.001%-10% w/v (10 µg/mL-100 mg/mL) |
|  | Non-aqueous Gel Polyethylene glycol 400 (20% to 35% (w/w)) Propylene glycol (65% to 80% (w/w)) Cellulose derivative (0.5% to 5.0% (w/w)) | 10%-25% w/v |
|  | Water or saline | up to 100% w/v |
| 3 | GML | 0.001%-10% w/v (10 µg/mL-100 mg/mL) |
|  | Non-aqueous Gel Polyethylene glycol 400 (20% to 35% (w/w)) Propylene glycol (65% to 80% (w/w)) Cellulose derivative (0.5% to 5.0% (w/w)) | 10%-25% w/v |
|  | Water or saline | 1% to 25% w/v |
|  | Vegetable oil | up to 100% w/v |
| 4 | GML | 0.001%-10% w/v (10 µg/mL-100 mg/mL) |
|  | Non-aqueous Gel Polyethylene glycol 400 (20% to 35% (w/w)) Propylene glycol (65% to 80% (w/w)) Cellulose derivative (0.5% to 5.0% (w/w)) | 10%-25% w/v |
|  | Vaseline | up to 100% w/v |
| 5 | GML | 5% w/v |
|  | Non-aqueous Gel Polyethylene glycol 400 (25% (w/w)) Propylene glycol (73.55% (w/w)) Cellulose derivative (1.25% (w/w)) | 10% w/v |
|  | Water | 85% w/v |
| 6 | GML | 100 µg/mL |
|  | Vegetable oil | up to 100% w/v |

In one aspect, the present invention provides a method of treating a microbial infection in a subject in need thereof. The microbial infection, in one embodiment, is a bacterial, viral, or fungal infection, or a combination thereof.

Without wishing to be bound by theory, the GML topical compositions described herein are less irritating than currently approved antimicrobial compositions, therefore resulting in a more favorable patient compliance rate, as compared to other antimicrobial compositions presently used in the art.

In one embodiment, the method comprises administering to the subject a topical composition comprising GML or a derivative thereof, as described herein. In one embodiment, the method comprises topically administering to the subject an effective amount of a composition comprising GML or a derivative thereof (e.g., a compound of one of Formulae I-VI), a vegetable oil, and a pharmaceutically acceptable topical carrier. In another embodiment, the method comprises topically administering an effective amount of a composition comprising GML, a non-aqueous gel, and a pharmaceutically acceptable topical carrier. In yet another embodiment, the method comprises administering to the subject one of the compositions provided in Table 1.

In one embodiment, the method of treating a microbial infection comprises applying an effective amount of one or more of the GML compositions described herein to at least one skin or mucosal surface of a subject.

In some embodiments, the composition is applied to or impregnated in a wipe, sponge, swab, or other material, and then applied to the skin or mucosal surface of the subject using the respective material. As used herein, the term "swab" refers to a material suitable for applying a liquid, gel, wax, cream, or lotion to a skin or mucosal surface, or the act of applying a liquid, gel, wax, cream, or lotion to the skin or mucosal surface, or the act of collecting a liquid, gel, wax, cream, lotion, or fluid from the skin or mucosal surface. In some embodiments, the material is attached to a holder, for example a stick, wire, rod, or applicator. In further embodiments, the material attached to a holder is attached at one or both ends thereof. In some embodiments, the wipe, sponge, swab, or other material is pre-loaded or packaged together with the composition.

Certain bacteria have been shown to be resistant to GML's antibacterial effect. Such bacteria include those with a dense LPS layer e.g., species of Enterobacteriaceae for example, *E. coli*, as well as *Pseudomonas aeruginosa*. In addition, the antimicrobial activity of GML can be inhibited by the production of lipases or other hydrolyse enzymes such as the esterase GEH, which is produced by *S. aureus*.

Without wishing to be bound by theory, it is thought that GML inhibits microbial infection through one or more of several mechanisms that include, but are not limited to, direct microbial toxicity; inhibiting entry of the infectious microorganism into the vertebrate cell; inhibiting growth of the microorganism; inhibiting production or activity of virulence factors such as toxins; stabilizing the vertebrate cells; or inhibiting induction of inflammatory or immunostimulatory mediators that otherwise enhance the infectious process.

Bacteria use two-component signal transduction systems to respond and adapt to environmental changes as well as produce virulence factors. Without wishing to be bound by theory, GML is believed to interfere with bacterial signal transduction, either directly or indirectly, through interaction with bacterial plasma membranes. In one embodiment, GML's bactericidal effect is mediated at least in part by interactions at the bacterial plasma membrane. In a further embodiment, GML can be detected in association with the bacterial plasma membrane, but cannot be detected in association with the cytoplasm.

In one embodiment, direct GML-mediated interruption of bacterial membranes includes interference with the localization of signaling proteins within the membrane, or interference with ligand binding to signaling proteins. In one embodiment, GML has an indirect effect on a two-component signal transduction system and the effect is selected from modifications to membrane structure that interfere with the ability of transmembrane proteins to perform signaling functions; dissipation of the bacterial plasma membrane potential; and alterations of pH gradients across the membranes.

In one embodiment, the indirect effect described above is mediated through one or more tetramic acids, for example those produced by *P. aeruginosa* and certain *lactobacillus* strains. Tetramic acids made by these organisms contain a 2,4 pyrrolidinedione ring and a 12 carbon side chain. Their properties include broad spectrum antibacterial effects and anti-inflammatory activities. Without wishing to be bound by theory, mechanistic similarities between tetramic acids and GML may explain why *P. aeruginosa* and lactobacilli are highly resistant to GML antimicrobial activities. For *P. aeruginosa*, tetramic acids are important for the homoserine lactone quorum sensing system. For example, *P. aeruginosa* grown in the presence of high concentrations of GML (>2000 µg/ml) at pH 7.0 appears to have up-regulated production of numerous virulence factors including pigments, consistent with effects associated with activation of the quorum sensing system.

Exemplary two-component systems found in *S. aureus* include the agr regulatory system and WalK/R. It has been shown that GML affects the agr regulatory system, which regulates several virulence factors in *S. aureus*. WalK/R is essential for microbial viability. Without wishing to be bound by theory, one or more two-component systems critical for microbial viability such as WalK/R, for example, may be directly inhibited by GML at higher doses, resulting in rapid death of the microbes.

Similar to GML's putative effects on bacterial plasma membranes, GML has been shown to inactivate certain viruses by disrupting viral lipid envelopes [Thormar et al. (1994) Ann NY Acad Sci 724; 465].

In one embodiment, the methods described herein are used to treat a patient with a vaginal microbial infection. In a further embodiment, the vaginal microbial infection is vulvovaginal candidiasis (VVC) or bacterial vaginosis (BV). Women with BV are at risk for pelvic inflammatory disease, endometritis, and vaginal cuff cellulitis, and pregnant women with BV are at further risk of low birth weight, pre-term labor, pre-term delivery, and chorioamnionitis. In patients with VVC or BV, the vaginal flora, which is normally dominated by *Lactobacillus* species, becomes altered such that other bacterial and/or fungal species dominate. *Gardnerella vaginalis* and other anaerobic bacteria are commonly associated with BV; *Candida* species, usually *C. albicans*, are associated with VVC. Accordingly, in one embodiment, the methods provided herein are used to treat a patient with an anaerobic bacterial infection. In a further embodiment, the infection is a *Gardnerella vaginalis* or *Candida* infection (e.g., *C. albicans*).

The GML compositions provided herein, in one embodiment, are used in methods to inhibit the production of toxins. For example, in one embodiment, a method is provided to inhibit a bacterial toxin and/or reduce illness associated with a bacterial toxin. In a further embodiment, the method comprises applying one or more of the topical compositions described herein to a tampon or wound dressing, which is subsequently used by the subject, or applied to the subject. In a further embodiment the bacterial illness treated by the methods described herein is Toxic Shock Syndrome (TSS), which is caused by production of TSS toxin 1 (TSST-1) or, more rarely, other toxins such as enterotoxin A, B, and C, by *S. aureus*. The symptoms and sequelae of TSS may include an acute fever, rash, hypotension, malaise, multiple organ failure, coma, desquamation of the skin, or death. Most cases of TSS are associated with the use of tampons during menstruation, although TSS can occur in any individual with a *S. aureus* infection, particularly an individual with a skin wound.

Urinary tract infections (UTIs) are particularly common in women and elderly individuals. UTIs typically begin in the lower urinary tract (i.e., the urethra and bladder), and are generally treated with antibiotics after the onset of symptoms. If left untreated, a UTI can spread to the kidney and result in permanent kidney damage. UTIs are typically caused by *Escherichia coli*, but can also be caused by other Enterobacteriaceae, *Staphylococcus aureus*, other gram positive bacteria or, more rarely, viruses or fungal species. In one embodiment, the methods described herein are used to treat a subject having a urinary tract infection. The method comprises, in one embodiment, topically applying to a skin or mucosal surface of the patient, one or more of the compositions described herein. In a further embodiment, the patient has undergone long-term antibiotic therapy prior to the topical application of the composition.

In order to establish infection in a host subject, viruses such as HIV and SIV are believed to require an initial inflammatory response that results in recruitment of CD4+ T cells which are subsequently infected by the virus, to the site of infection. In one embodiment, the methods described herein are used to treat HIV and/or SIV infections. The method comprises, in one embodiment, topically applying to a skin or mucosal surface of the patient, one or more of the compositions described herein. In a further embodiment, the composition is administered intra-vaginally.

It is estimated that there are more than 500,000 cases of post-surgical *S. aureus* infections yearly in the United States, and it has been shown that 80% of such infections result from the same bacterium that is found in patients' anterior nares. Additionally, there have been significant outbreaks of streptococcal pharyngitis and streptococcal toxic shock syndrome associated with upper respiratory tract infection with *Streptococcus pyogenes*, for example an outbreak of the M3 strain. These facts suggest that nasal decolonization, when combined with possible decolonization of other parts of the upper respiratory tract and use of surgical scrubs that kill pathogens on surgical sites, may be effective in preventing and treating post-surgical infections and other respiratory tract infections. In some embodiments, the GML compositions provided herein are used in methods to decolonize the respiratory tract, other mucosal surfaces, or surgical incision sites in order to reduce streptococcal pharyngitis, streptococcal toxic shock syndrome or post-surgical *S. aureus* infections. In some embodiments, the method comprises applying one or more of the compositions provided herein to the anterior nares of a subject. For example, in one embodiment, 1 mg/mL GML in a 10% non-aqueous gel is applied to a swab and the swab is rotated around each nare up to the nasal bone 3 times.

It has been reported that oral streptococci are implicated in gum disease and dental caries, and, in susceptible individuals, infective endocarditis. The GML compositions provided herein are used in some embodiments to prevent or treat streptococcal infections that lead to dental caries, gum disease, and infective endocarditis. The method in one embodiment comprises applying to the teeth and gum lines of a subject one or more of the compositions provided herein. For example, in one embodiment, 1 mg/mL GML in a 5% non-aqueous gel is applied to the teeth and gum lines of a subject using a swab.

In some embodiments, the subject has a bacterial infection. Bacterial infections that are treatable with the topical compositions provided herein include, but are not limited to, infections caused by the following bacteria: Staphylococci (e.g., *S. aureus, S. intermedius, S. epidermidis*), Group A *Streptococcus* (e.g., *S. pyogenes*), Group B *Streptococcus* (e.g., *S. agalacticae*), Groups C, F, and G *Streptococcus, Streptococcus pneumoniae, Bacillus anthracis, Peptostreptococcus* species, *Clostridium peifringes, Neisseriae gonorrheae, Chlamydia trachomatis, Haemophilus influenzae, Pseudomonas aeruginosa, Helicobacter pylori, Gardnerella vaginalis, Bacteroides fragilis, Burkholderia cepacia, Bordatella bronchiseptica, Campylobacter jejuni*, Enterobacteriacae (e.g., *Escherichia coli*) *Pasteurella multocida*, and *Mycobacterium* (e.g., *M. tuberculosis* and *M. phlei*).

Additionally, the topical compositions described herein, in one embodiment, are used to treat one or more bacterial infections caused by one or more of the bacteria listed in Table 2. Table 2 shows the results of experiments testing the anti-bacterial activity of GML against various bacteria grown under optimal growth conditions. *Burkholderia cenocepacia*, which used to be named *Pseudomonas cepacia* and is related to *Pseudomonas aeruginosa*, was killed by GML at concentrations of 500 µg/mL. Mycobacterial species typically produce large amounts of complex fatty acids. However, these organisms were killed by GML at concentrations of ≥50 µg/mL. In addition to inhibiting the growth gram-positive bacteria, GML inhibited exotoxin production independently from inhibition of growth for all such organisms tested (*Staphylococcus aureus, Streptococcus pyogenes, Streptococcus agalactiae*, groups C, F, and G streptococci, and *Clostridium perfringens*). The most susceptible organisms to killing by GML were *Peptostreptococcus* species, *Clostridium perfringens, Bordetella bronchiseptica*, and *Campylobacter jejuni*, all of which were killed by GML (1 µg/mL).

TABLE 2

Spectrum of antibacterial activity of GML

| Bacterium | Gram or Other Stain | Oxygen Tolerance | Strains Tested | Average Bactericidal Concentration of GML (µg/ml) |
|---|---|---|---|---|
| *Staphylococcus aureus* | Positive | Aerobe | 54 | 300 |
| *Streptococcus pyogenes* | Positive | Aerotolerant Anaerobe | 4 | 30 |
| *Streptococcus agalactiae* | Positive | Aerotolerant Anaerobe | 3 | 30 |
| Group C *Streptococcus* | Positive | Aerotolerant Anaerobe | 1 | 30 |
| Group F *Streptococcus* | Positive | Aerotolerant Anaerobe | 1 | 20 |
| Group G *Streptococcus* | Positive | Aerotolerant Anaerobe | 1 | 50 |
| *Streptococcus suis* | Positive | Aerotolerant Anaerobe | 1 | 50 |
| *Streptococcus sanguinis* | Positive | Aerotolerant Anaerobe | 1 | 50 |
| *Streptococcus pneumoniae* Serotype III | Positive | Aerotolerant Anaerobe | 2 | 10 |
| *Enterococcus faecalis* | Positive | Aerotolerant Anaerobe | 1 | 100 |
| *Listeria monocytogenes* | Positive | Aerobe | 1 | 50 |
| *Bacillus anthracis* Sterne | Positive | Aerobe | 1 | 50 |
| *Bacillus cereus* | Positive | Aerobe | 1 | 50 |
| *Peptostreptococcus* species | Positive | Anaerobe | 1 | 1 |
| *Clostridium perfringens* | Positive | Anaerobe | 1 | 1 |
| *Neisseria gonorrhoeae* | Negative | Aerobe | 1 | 20 |
| *Haemophilus influenzae* Non-typable | Negative | Aerobe | 2 | 50 |
| *Gardnerella vaginalis* | Negative | Aerobe | 2 | 10 |
| *Campylobacter jejuni* | Negative | Aerobe | 1 | 1 |
| *Bordetella bronchiseptica* | Negative | Aerobe | 1 | 1 |
| *Pseudomonas aeruginosa* | Negative | Aerobe | 1 | Not Susceptible |
| *Burkholderia cenocepacia* | Negative | Aerobe | 1 | 500 |
| *Pasteurella multocida* | Negative | Aerobe | 1 | 500 |
| *Prevotella melaninogenica* | Negative | Anaerobe | 1 | 50 |
| *Bacteroides fragilis* | Negative | Anaerobe | 2 | 50 |
| *Fusobacterium* species | Negative | Anaerobe | 1 | 50 |
| *Escherichia coli* | Negative | Aerobe | 2 | Not Susceptible |
| *Salmonella minnesota* | Negative | Aerobe | 1 | Not Susceptible |
| *Enterobacter aerogenes* | Negative | Aerobe | 1 | Not Susceptible |
| *Proteus vulgaris* | Negative | Aerobe | 1 | Not Susceptible |
| *Shigella sonni* | Negative | Aerobe | 1 | Not Susceptible |
| *Klebsiella pneunoniae* | Negative | Aerobe | 1 | Not Susceptible |
| *Mycobacterium phlei* | Acid Fast | Aerobe | 1 | 100 |
| *Mycobacterium tuberculosis* | Acid Fast | Aerobe | 1 | 100 |
| *Mycoplasma hominis* | Cell Wall deficient | Aerobe | 1 | 1 |

In some embodiments, the subject to be treated with one or more of the topical compositions provided herein has a viral infection. In a further embodiment, the viral infection is caused by one or more of the following viruses, or class of viruses: influenza virus, herpesviruses (e.g., Herpes Simplex Virus 2), lentiviruses (e.g., Human Immunodeficiency virus).

In some embodiments, the subject to be treated with one or more of the topical compositions provided herein has a fungal infection. In a further embodiment, the fungal infection is caused by one or more of the following organism species: *Candida* species (e.g. *C. albicans*), *Microsporum* species, *Trichophyton* species, *Epidermophyton floccosum, Penicillium* species, *Aspergillus* species, *Trichomonas vaginalis*.

Methods of identifying and diagnosing a bacterial, viral, or fungal infection are generally known by those skilled in the art. To assess whether the formulations disclosed herein are useful to treat an infection, methods known to those of ordinary skill in the art may be employed. For example, a BV infection prior to, and after treatment, may be assessed by microscopic examination of vaginal cells.

In one embodiment, a method is provided to remove or kill a biofilm comprising one or more microorganisms. Biofilms can be involved in UTIs, ear infections, and dental diseases such as gingivitis, and can also form on the surface of implanted devices including prostheses, catheters, or heart valves. In one embodiment, the method comprises administering the topical composition by applying it directly to the biofilm.

In some embodiments, the methods of the invention comprise administering a second active agent, along with GML or a derivative of GML. The additional active agent may be present in the compositions described herein, or may be administered separately. In one embodiment, the one or more additional active agents prior to, or after, the topical GML composition is administered. For example, the two active agents may be topically administered serially, or administered serially by different routes of administration.

In one embodiment, the additional active agent(s) is administered before, during, or after administration of the composition of the invention. In another embodiment, the additional active agent(s) is administered by the same route as the composition or by a different route. For example, the additional active agent(s), in one embodiment, is administered by one of the following routes of administration: topical, intranasal, intradermal, intravenous, intramuscular, oral, vaginal, rectal, otic, ophthalmic, subcutaneous. The dose of additional active agents depends on, for example, the nature of the infection or illness; the site of administration; subject weight, age, sex, and surface area; concomitant medications; and medical judgment.

Additional active agents include, for example, antibiotics, anti-viral agents, and anti-fungal agents. Antibiotics include, without limitation, aminoglycosides, carbacephems, cephalosporins, glycopeptides, lincosamides, lipopetides, macrolides, monobactams, nitrofurans, penicillins, polypetides, quinolones, sulfuramides, and tetracyclines. Anti-fungal agents include, without limitation, those of the azole class, polyene class, or echinocanins class, nucleoside analogues, allylamines, griseofulvin, tolnaftate, or selenium compounds. Anti-viral agents include, for example and without limitation, acyclovir, ganciclovir, valganciclovir, abacavir, enofovir, lamivudine, emtricitabine, zidovudine, tenofovir, efavirenz, raltegravir, enfuvirdide, maraviroc, ribavirin, amantadine, rimantadine, interferon, oseltamivir, and zanamivir.

EXAMPLES

The present invention is further illustrated by reference to the following Examples. However, it should be noted that these Examples, like the embodiments described above, are illustrative and are not to be construed as restricting the scope of the invention in any way.

Example 1. Antimicrobial Effects of GML in Vegetable Oil

A study was undertaken to assess the ability of various concentrations of GML in olive, palm, or corn oil to inhibit the growth of several bacterial or fungal microorganisms in vitro.

Figure 2:
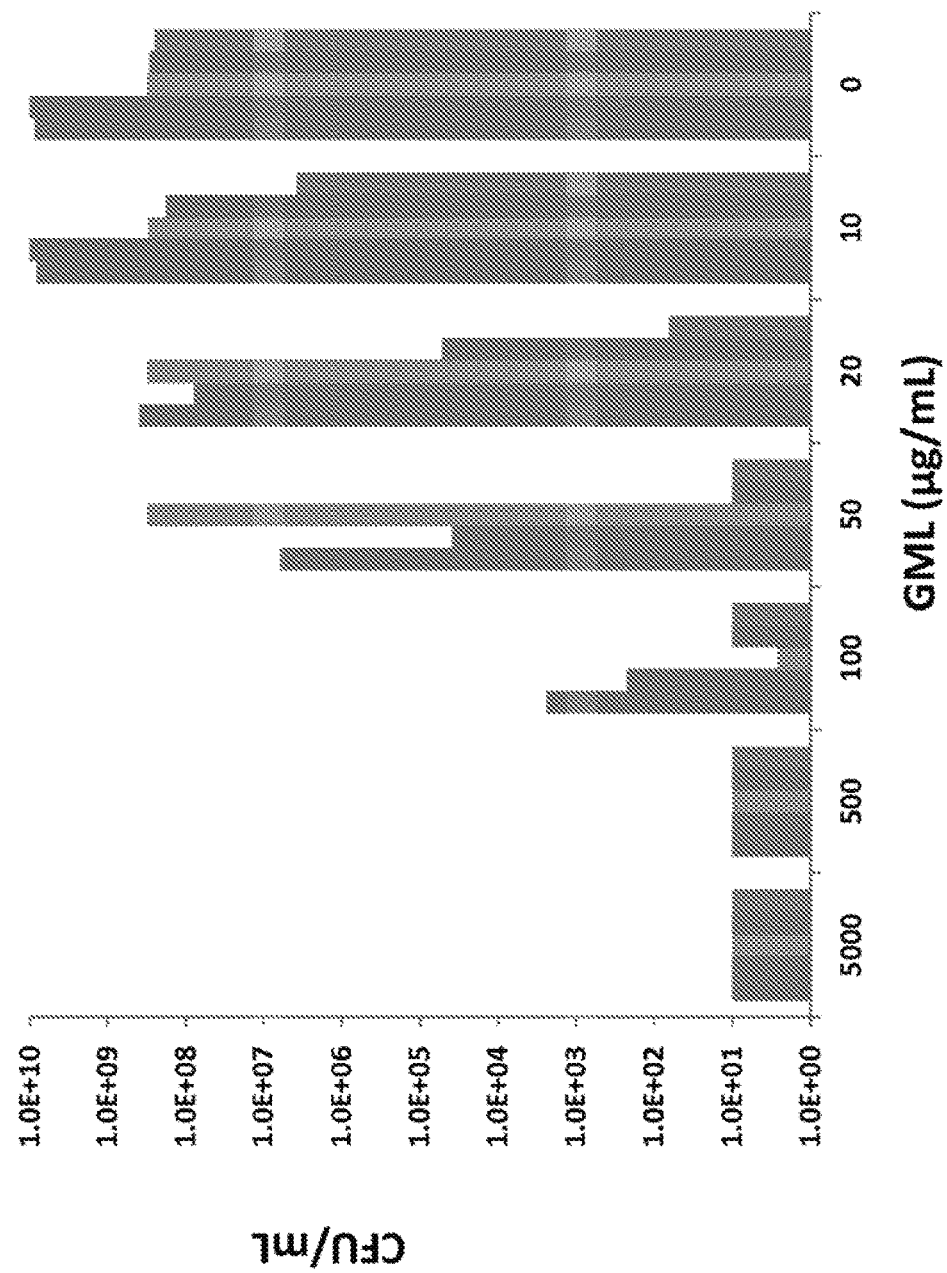
FIG. 2 is a graph showing the effect of various concentrations of GML in palm oil on the growth of several microorganisms (measured as CFU/mL). Bars represent the following microorganisms, from left: *Staphylococcus aureus* MNPE (methicillin sensitive strain), *S. aureus* MW2 (methicillin resistant strain), *Candida albicans*, *Streptococcus agalactiae*, and *Gardnerella vaginalis*.
Figure 3:
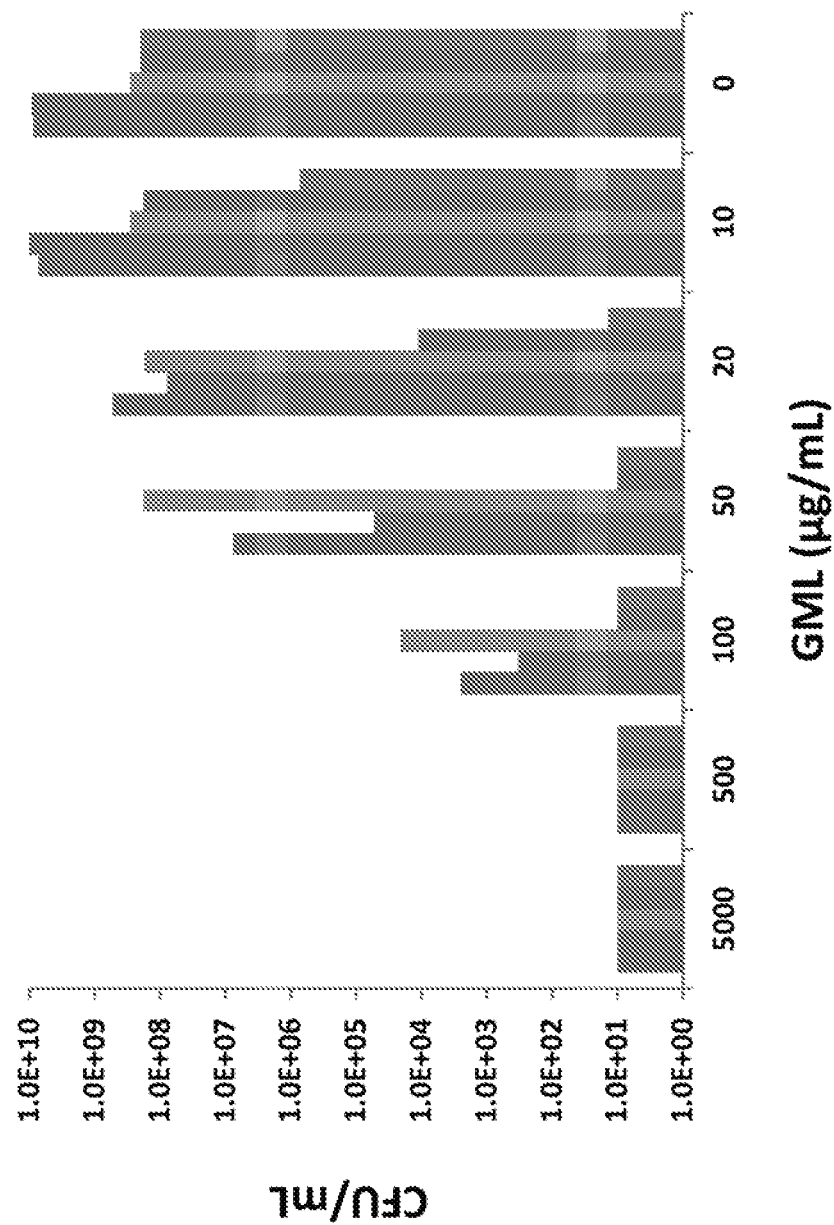
FIG. 3 is a graph showing the effect of various concentrations of GML in corn oil on the growth of several microorganisms (measured as CFU/mL). Bars represent the following microorganisms, from left: *Staphylococcus aureus* MNPE (methicillin sensitive strain), *S. aureus* MW2 (methicillin resistant strain), *Candida albicans*, *Streptococcus agalactiae*, and *Gardnerella vaginalis*.

GML in olive (FIG. 1), palm (FIG. 2), or corn (FIG. 3) oil was pre-warmed to 37° C. to melt the GML and was then added to 1 mL of Todd Hewitt (Difeo, Detroit MI) broth in round bottom tubes at concentrations ranging from 10 μg/mL to 5000 μg/mL. The following microbes were added to the tubes at the indicated concentrations: *Staphylococcus aureus* MNPE (methicillin sensitive, 1×107/mL); *Staphylococcus aureus* MW2 (methicillin resistant, 1×107/mL); *Streptococcus agalactiae* (1×107/mL); *Gardnerella vaginalis* (1×107/mL); or *Candida albicans* (1×106.)

The tubes were shaken at 37° C. at 200 revolutions per minute (RPM) in standard air for 18 hours. Plate counts were performed to determine colony-forming units/mL (CFU/mL).

In the presence of as little as 10 μg/mL GML, *G. vaginalis* CFU/mL were reduced in all three vegetable oils tested: growth of both *G. vaginalis* and *S. agalactiae* was completely or nearly completely inhibited at levels of 20 μg/mL GML or higher in all 3 vegetable oils tested. Additionally, the growth of *C. albicans* and both strains of *S. aureus* was inhibited at 100 μg/mL GML and growth was completely inhibited by GML at 500 μg/mL and 5000 μg/mL GML, in all 3 vegetable oils tested.

Thus, GML was effectively anti-microbial when mixed with olive, palm, or corn oil.

Example 2: Effect of GML on Microorganisms Growing as Biofilms

Figure 4:
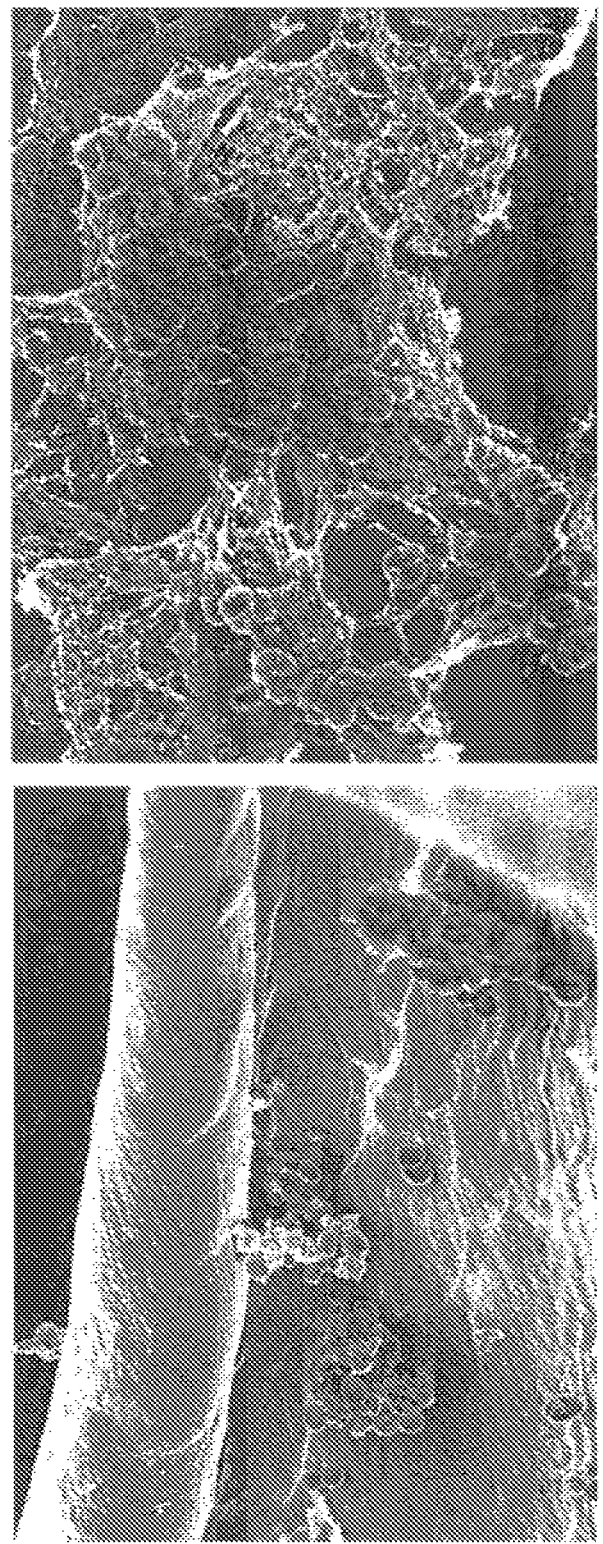
FIG. 4 is a set of scanning electron micrographs showing *S. aureus* growing as a biofilm on tampon fibers in cellulose acetate dialysis tubing at 6000× magnification (left) or 9000× magnification (right).

In order to assess the effect of GML on biofilms, *S. aureus* biofilms were grown. *S. aureus* 128, an organism that expresses toxic shock syndrome toxin-I (TSST-1), was inoculated at 107/0.1 mL onto the inside of pre-wetted dialysis tubing that had been tied off on one end. A tampon was then inserted into the dialysis tubing and the tubing was immersed under Todd Hewitt broth (Difeo Laboratories, Detroit, MI) containing 0.8% agar. The open end of the dialysis tubing remained above the agar surface such that the only source of nutrients for the growing microbes was media absorbed across the dialysis tubing. FIG. 4 shows biofilm growth on tampon fibers and cellulose acetate dialysis tubing after an 18 hour incubation, at 6000× (A) and 9000× (B) magnifications.

Figure 5:
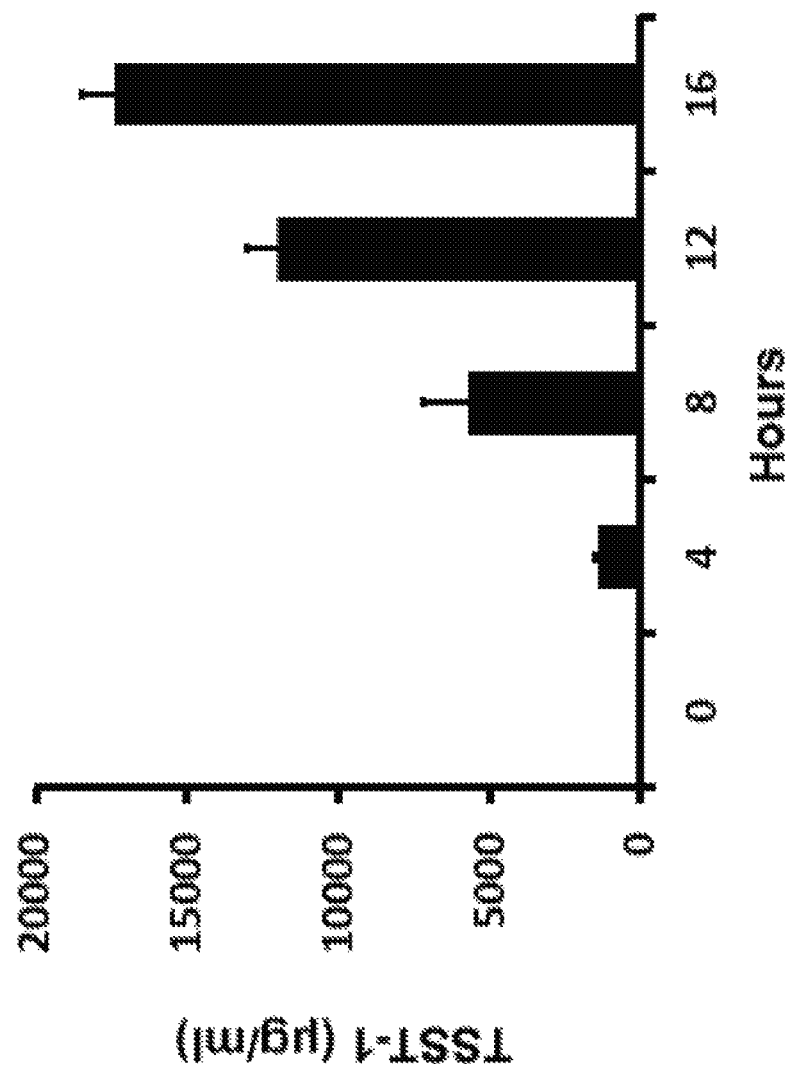
FIG. 5 is a graph showing the accumulation of the superantigen TSST-1 in biofilms grown on tampon fibers in cellulose acetate dialysis tubing.

Tampon sacs were incubated in the solidified agar. At 4, 8, 12, and 16 hours, tampon sacs were removed from the agar, sliced open, and weighed to determine fluid gain. TSST-1 was eluted by addition of phosphate-buffered saline (PBS). The accumulated amount of TSST-1 was quantified by first concentrating the eluted fluids by addition of 4 volumes of absolute ethanol, then resolubilizing in distilled water, and analyzing by Western immunoblot. FIG. 5 shows the increasing amounts of TSST-1 present in the tampons over time. TSST-1 was not detected in the presence of 5% GML (data not shown).

Figure 6:
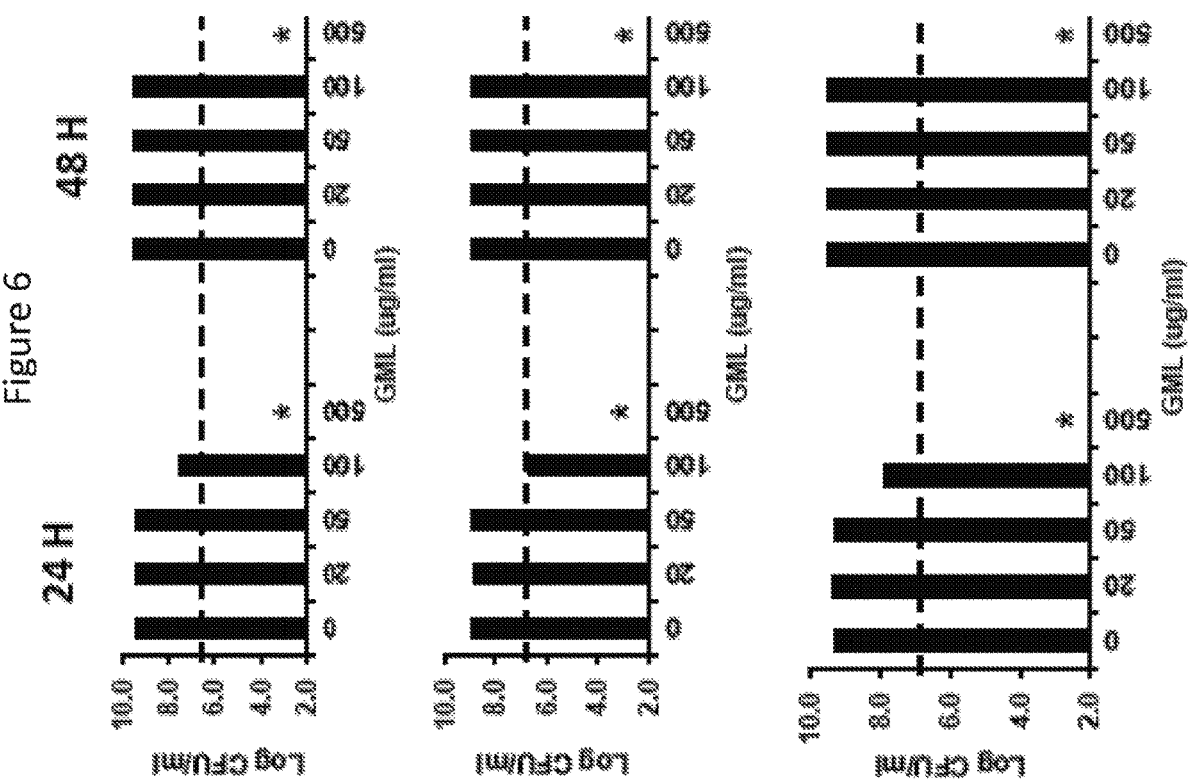
FIG. 6 is a series of graphs showing the measured CFU/mL from biofilms formed from *S. aureus* strains MN8 (methicillin sensitive strain, top panels), MNWH (methicillin resistant strain, middle panels), and MW2 (methicillin resistant strain, bottom panels) cultured in 96 well plastic microtiter plates, in the presence or absence of the indicated concentrations of GML for 24 or 48 hours.
Figure 7:
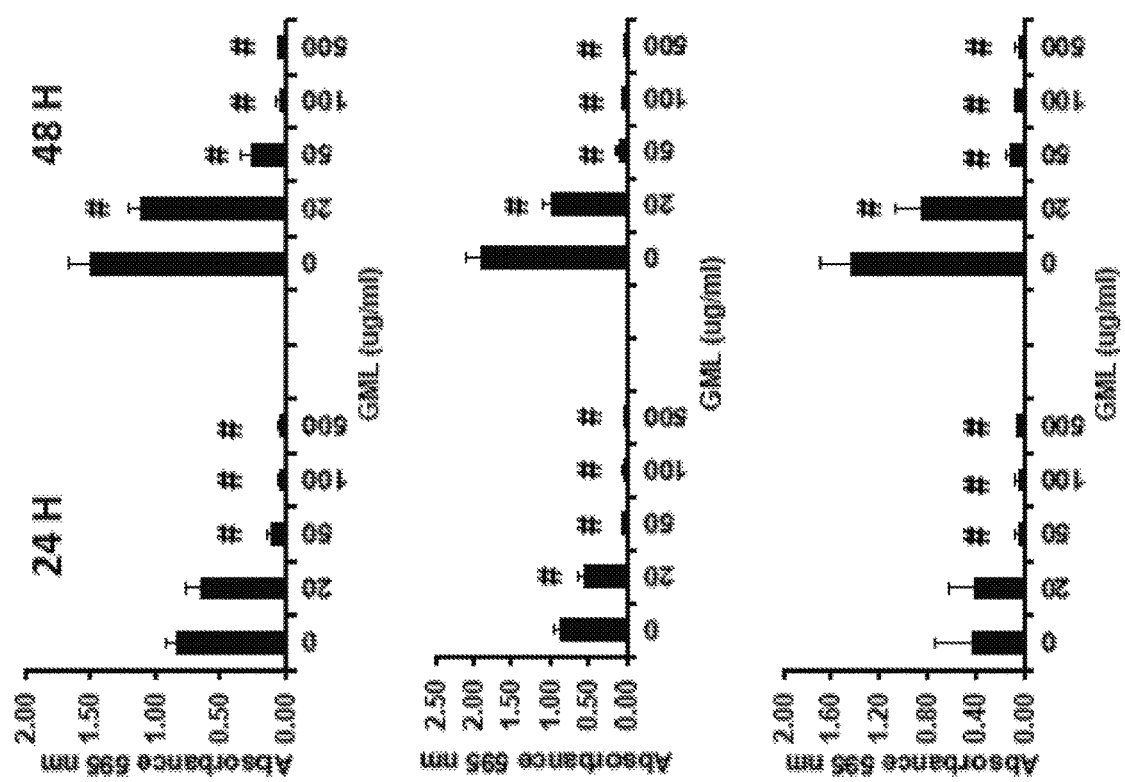
FIG. 7 is a series of graphs showing the measured biofilm absorbance at 595 nm after crystal violet staining of biofilms, formed from *S. aureus* strains MN8 (methicillin sensitive strain, top panels), MNWH (methicillin resistant strain, middle panels), and MW2 (methicillin resistant strain, bottom panels) cultured in 96 well plastic microtiter plates, for 24 or 48 hours, in the presence or absence of the indicated concentration of GML.
Figure 8:
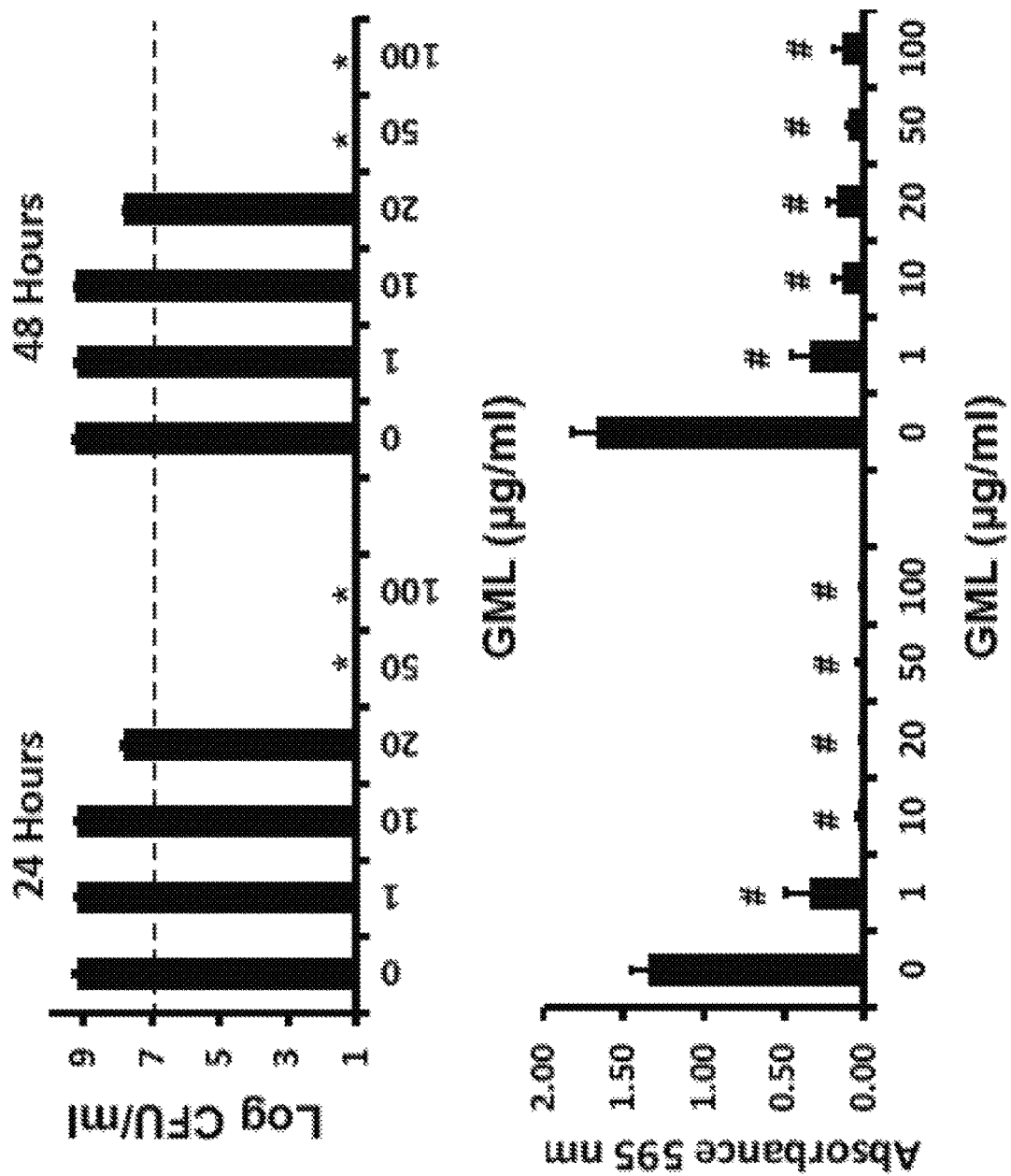
FIG. 8 is a set of graphs showing the measured CFU/mL (top) and absorbance at 595 nm after crystal violet staining (bottom) from *Haemophilus influenzae* biofilms cultured in 96 well plastic microtiter plates, for 24 or 48 hours, in the presence or absence of the indicated concentration of GML.

To directly assess the effect of GML on the formation of biofilms, 96 well plastic microtiter plates were inoculated with approximately 106/mL of one of three strains of *S. aureus* (MN8, a methicillin sensitive strain; MNWH, a methicillin resistant strain; or MW2, a methicillin resistant strain), or with non-typable *Haemophilus influenzae*. Wells were cultured stationary at 37° C. for 24 and 48 hours (FIGS. 6-8). As a control, in one set of three wells for each microbe, the wells were agitated 3 times by pipetting up and down. The bactericidal activity of GML was determined by measuring CFU/mL in supernatants. After removal of supernatants, wells were washed three times with PBS to remove unbound cells, and were then treated with crystal violet for 30 minutes. Wells were again washed three times with PBS to remove unbound crystal violet. Finally, wells were treated with ethanol to solubilize biofilm-associated crystal violet. Absorbances at 595 nm were determined by an ELISA reader to measure biofilm formation.

FIGS. 6, 7 and 8 provide the results of the study. Growth of all three *S. aureus* strains was completely inhibited by GML at 500 μg/mL at both 24 and 48 hours, as measured by CFU/mL (FIG. 6; dashed line indicates starting inoculum size; *significant reduction in mean CFU/mL compared to starting inoculum, p<0.001.). In contrast, at 10 fold lower GML concentrations than necessary to inhibit bacterial growth, biofilm formation was significantly inhibited as measured by reduced crystal violet staining of retained biofilm material in wells of the microtiter plates (FIG. 7; #significant reduction in mean absorbance at 595 nm compared to no GML wells, p<0.01).

Similarly, GML was bactericidal against non-typable *H. influenzae* in the context of a biofilm at concentrations of 50 μg/mL (FIG. 8, top; dashed line indicates starting inoculum size; *significant reduction in mean CFU/mL compared to starting inoculum, p<0.001). In addition, GML inhibited *H. influenzae* biofilm formation at concentrations as low as 1.0

µg/mL, as measured at 24 and 48 hours (FIG. 8, bottom; #significant reduction in mean absorbance at 595 nm compared to no GML control, p<0.01).

In order to assess the effect of GML on previously formed biofilms, side-by-side wells that were not treated with GML throughout the incubation and that had high absorbances at 595 nm at 48 hours, indicating that a biofilm had formed in the well, were treated with 500 µg/mL GML for 60 minutes at 37° C. Supernatants were removed and bactericidal activity was determined by measuring CFU/mL (FIG. 9, left; #significant reduction in mean absorbance at 595 nm compared to no GML control, p<0.01). Wells were then washed and stained with crystal violet as described above.

Figure 9:
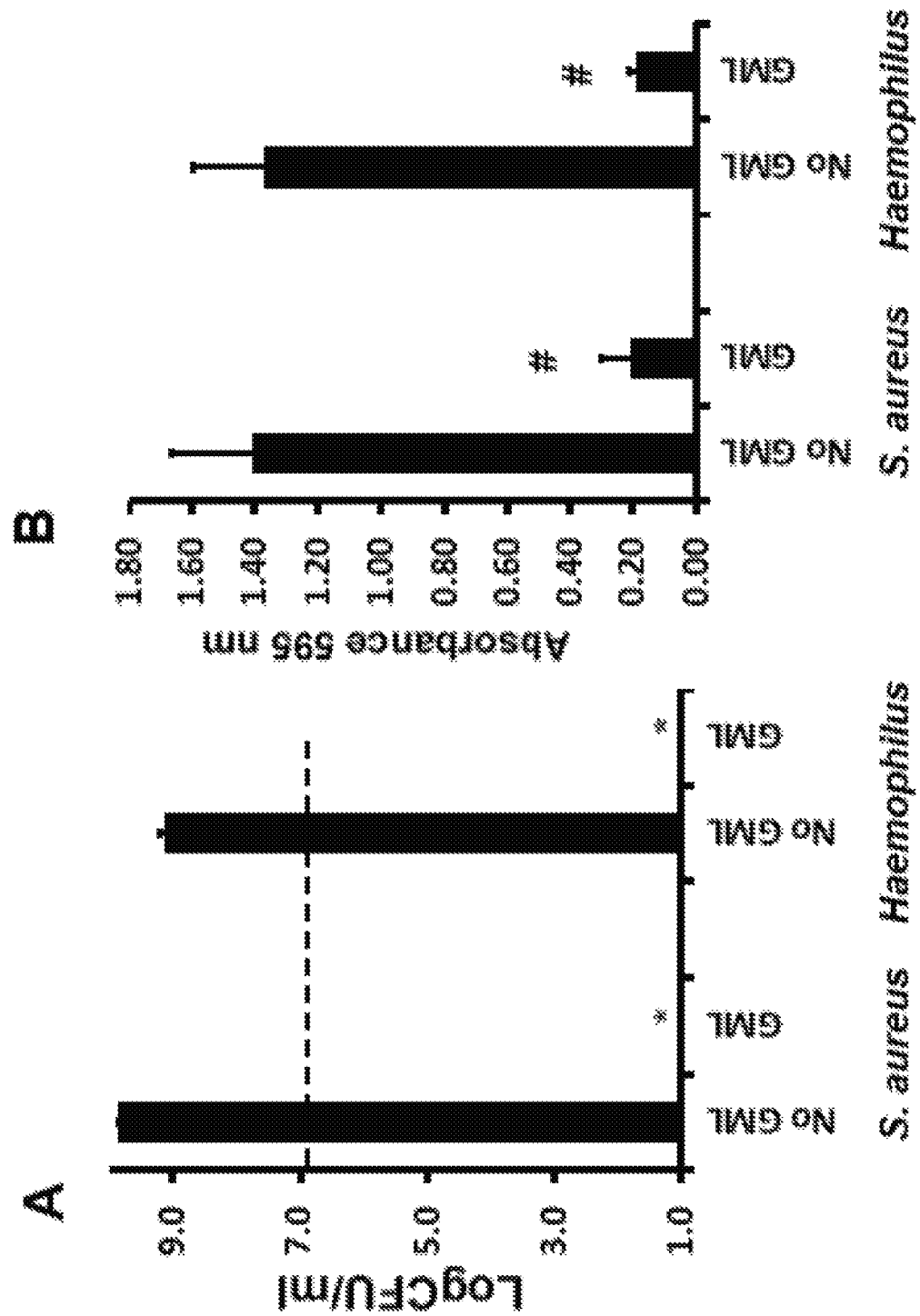
FIG. 9 is a set of graphs showing the measured CFU/mL (left) and absorbance at 595 nm after crystal violet staining (right) from *S. aureus* or *H. influenzae* biofilms treated with 500 g/mL GML.

FIG. 9 provides the results of the study. After 48 hours, 500 µg/mL GML killed both S. aureus and H. influenzae (FIG. 9, left). Similarly, 500 µg/mL GML nearly completely removed biofilm material attached to the wells as demonstrated by a loss of crystal violet staining in GML-treated wells (FIG. 9, right).

Example 3: Synergistic Effects of GML and EDTA on the Growth of E. coli

Previous studies indicated that Enterobacteriaceae species such as E. coli, as well as Pseudomonas aeruginosa, were resistant to GML's antibacterial effects, and suggested that the dense layer of LPS was protective from GML in these organisms. An additional study was undertaken to determine if the addition of EDTA to a GML composition would enhance the antimicrobial properties of the GML composition.

E. coli (Watson strain) was adjusted to 1.2×107/mL in Todd Hewitt media. Various concentrations of EDTA ranging from 0.05 M to 0.00005 M, in the presence or absence of 100 µg/mL GML, were added to the wells. Cultures were incubated with shaking (200 RPM) for 24 hours, at which time samples were removed for plate counting.

Figure 10:
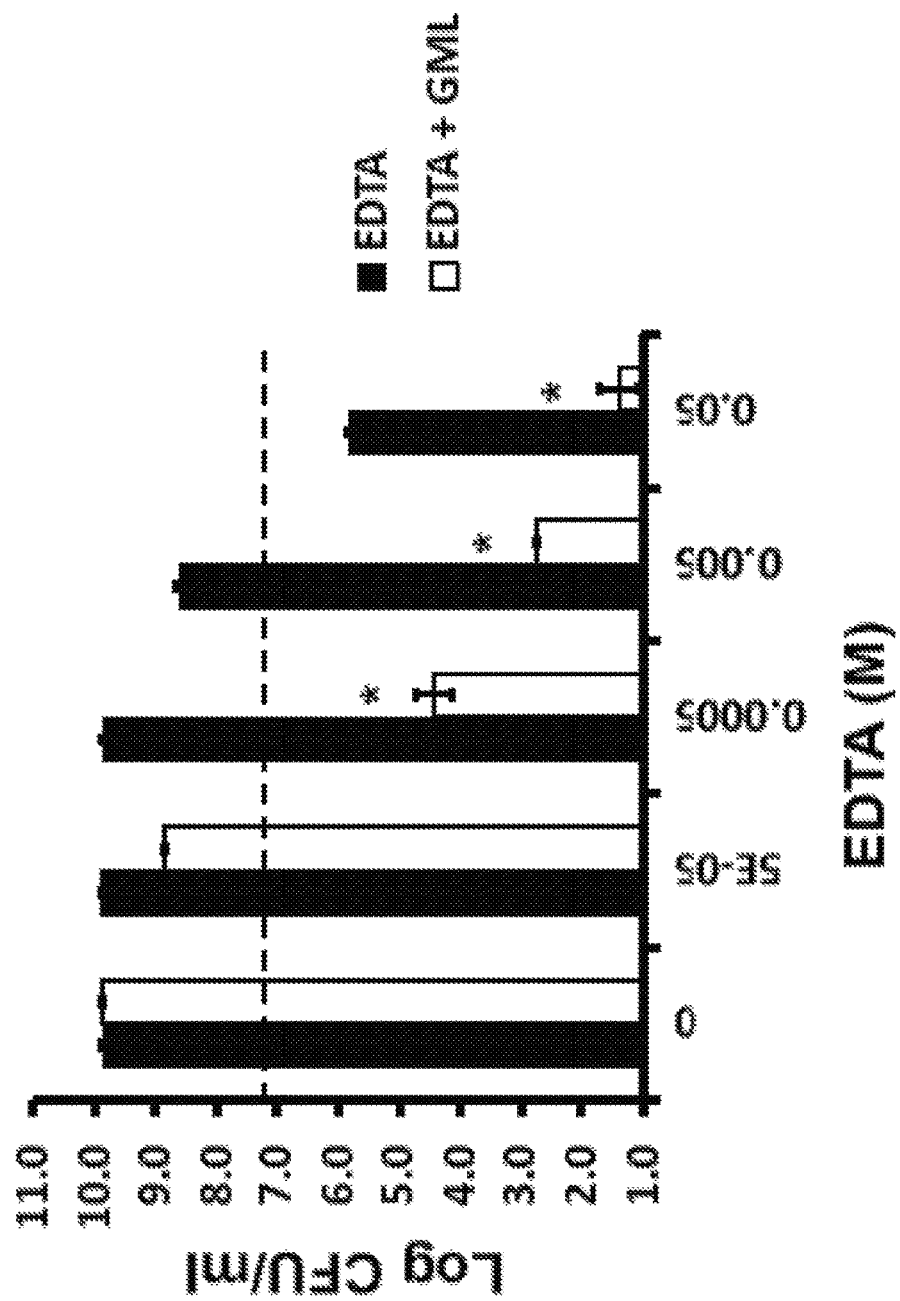
FIG. 10 is a graph showing CFU/mL from *E. coli* cultures grown for 24 hours in the presence or absence of 100 µg/mL GML, and in the presence of increasing concentrations of EDTA.

The results of the study are shown in FIG. 10. EDTA alone inhibited the growth of E. coli somewhat, in a dose-dependent manner. The combination of 100 µg/mL GML with EDTA showed increased anti-bacterial activity (*p<0.001; dashed line indicates starting inoculum size).

Figure 11:
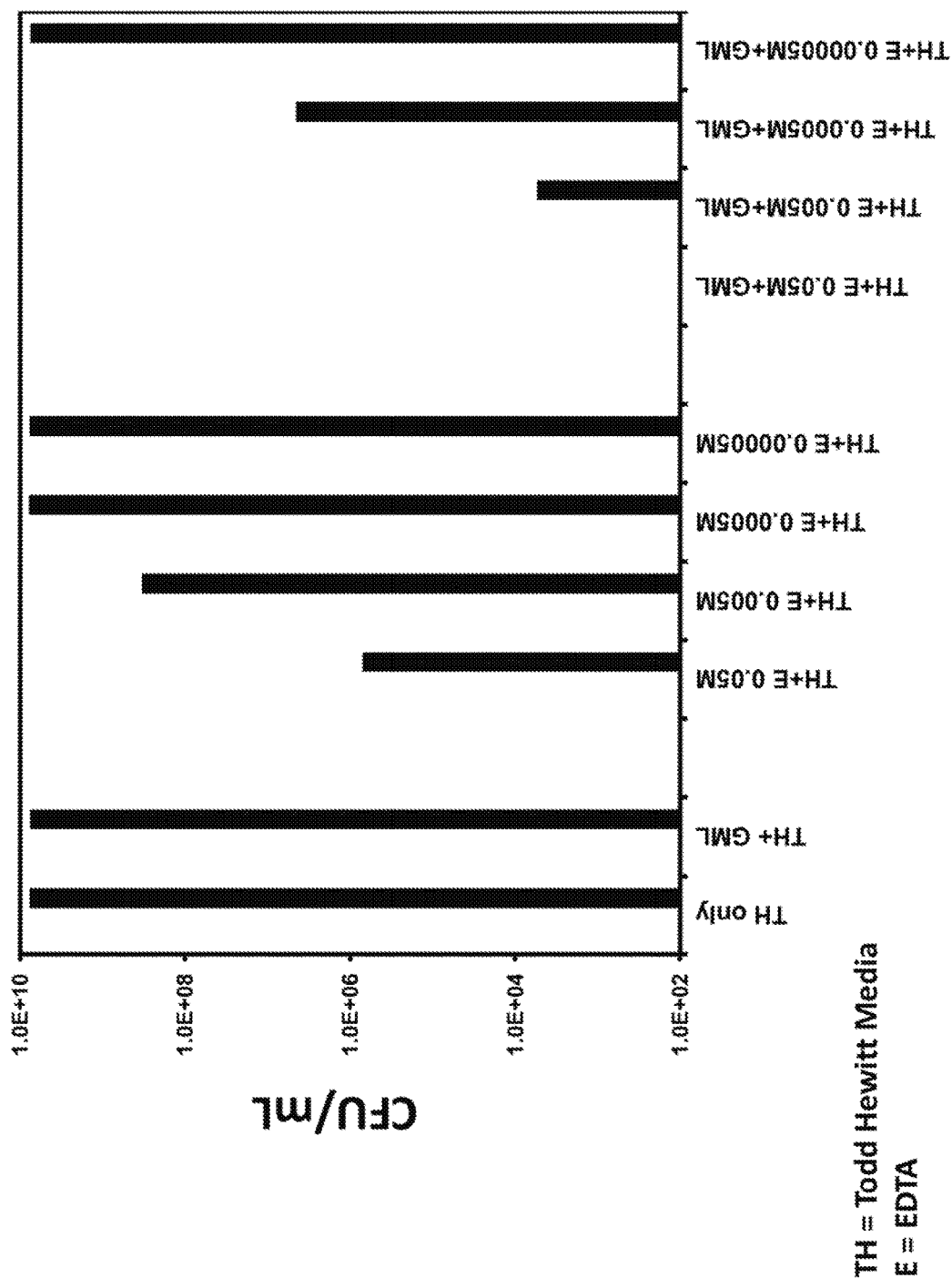
FIG. 11 is a graph showing CFU/mL from *E. coli* cultures grown for 24 hours in 100 µg/mL GML alone, increasing concentrations of EDTA alone, or increasing concentrations of EDTA in the presence of 100 µg/mL GML.

To further assess the combined effects of GML and EDTA, the experiment was carried out as above, and the relative effects on the growth of E. coli of EDTA alone or the combination of GML and EDTA were assessed in direct comparison to GML alone. The results are provided in FIG. 11. As in the experiment described above, EDTA alone inhibited the growth of E. coli to some extent at higher concentrations, while the combination of 100 µg/mL GML with EDTA showed increased anti-bacterial activity, in a dose-dependent fashion. GML alone did not exhibit any bactericidal activity against E. coli. Therefore, GML and EDTA exerted a synergistic anti-bacterial effect.

Example 4: The Effect of pH on GML Activity Against Pathogenic Microorganisms

Because the presence of EDTA made E. coli susceptible to GML, it was hypothesized that protonating the surface of E. coli or P. aeruginosa may increase GML activity through repelling divalent cations, thereby disrupting LPS integrity.

An experiment was conducted to determine the effect of GML in the presence of various pH levels on the growth of E. coli. E. coli (Watson strain) was grown in Todd Hewitt media and adjusted to 107 CFU/mL. Using acetate buffer, the pH of the cultures was adjusted to 5.0, 6.0, or 7.0. GML was added to cultures at concentrations of 5000, 50, or 0.1 µg/mL, and cultures were incubated at 37° C. with shaking (200 RPM). Samples were removed for enumeration of CFU/mL at 24 hours.

Figure 12:
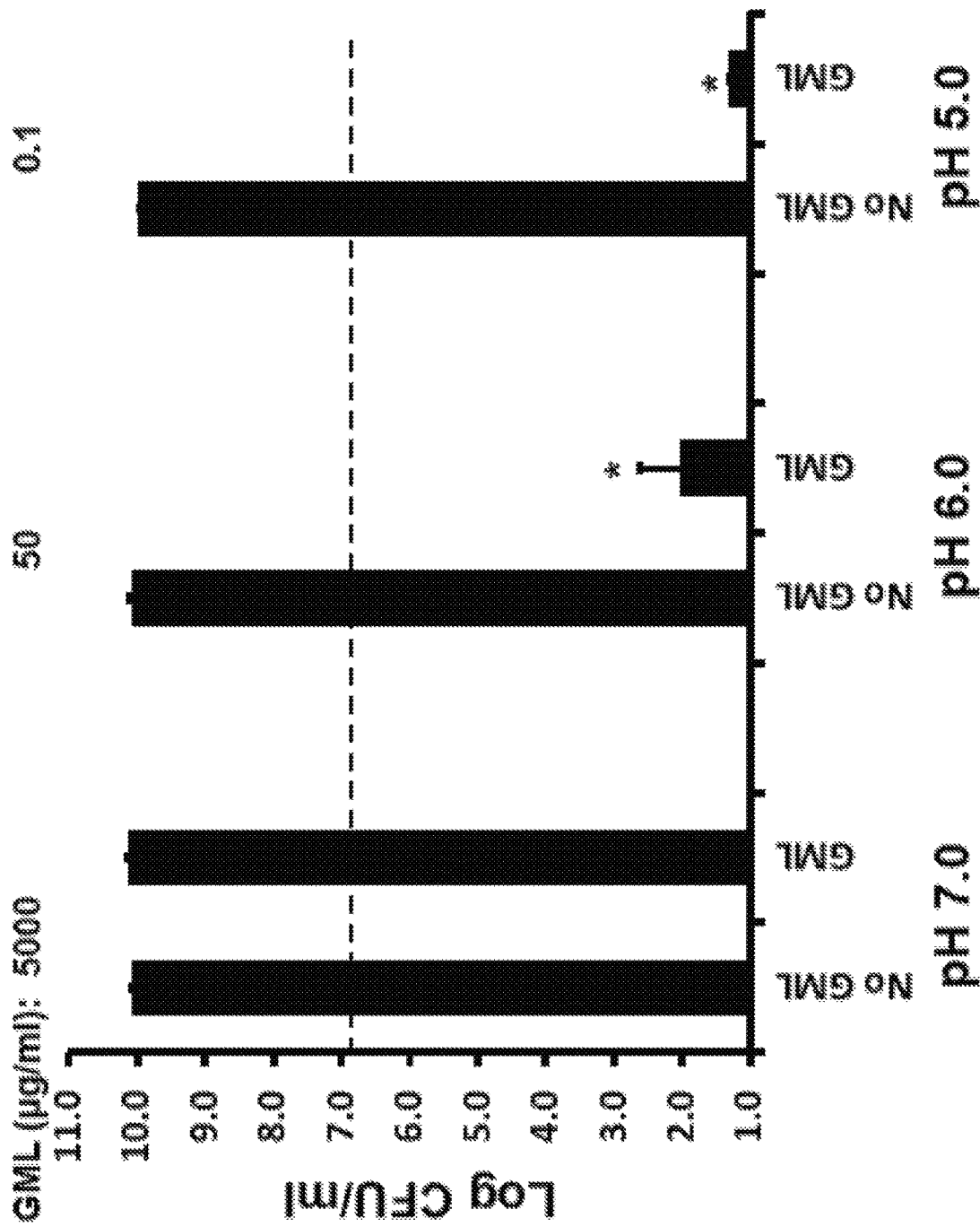
FIG. 12 is a graph showing CFU/mL from *S. aureus* cultures grown at the indicated pH and at the indicated concentrations of GML.

The results of the study are provided in FIG. 12. E. coli was not susceptible to GML at pH 7.0, even when as much as 5000 µg/mL GML was added to the culture. However, E. coli was highly susceptible to GML at a pH of 6.0, as 50 µg/mL GML was bactericidal, and was even more susceptible to GML at pH 5.0, as only 0.1 µg/mL GML was bactericidal in these cultures. With each unit drop in pH, E. coli appeared to become 500 times more susceptible to GML. (*p<0.001; dashed line indicates starting inoculum size).

A similar experiment was carried out to assess the effect of GML on the growth of Haemophilus influenzae at various pHs. 1 µg/mL GML had no effect on the growth of H. influenzae at a pH of 7.0 (FIG. 13). However, at a pH of 6.0, 1 µg/mL GML completely abrogated the growth of H. influenzae at 4, 8, and 24 hours (FIG. 13).

Figure 14:
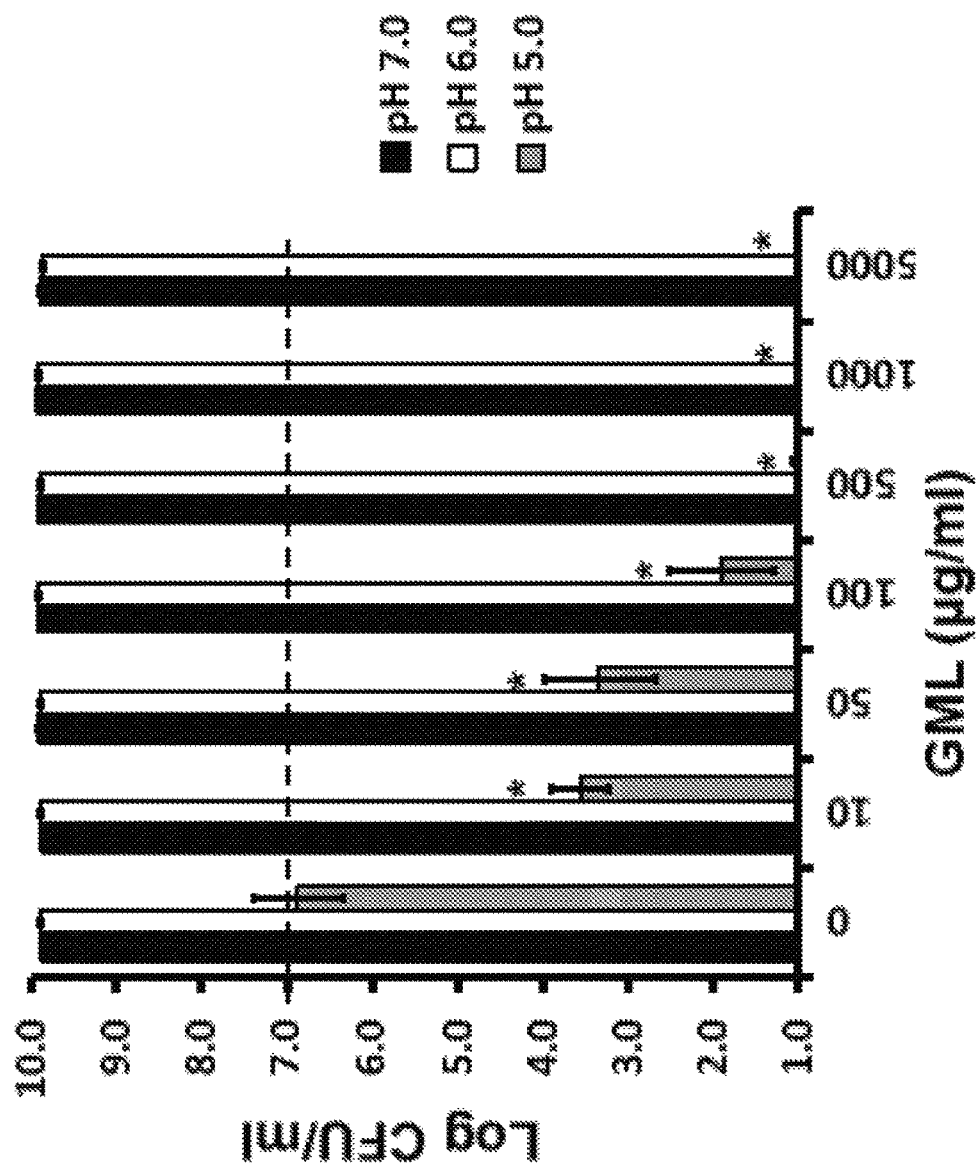
FIG. 14 is a graph showing CFU/mL from *Pseudomonas aeruginosa* cultures grown at the indicated pH and at the indicated concentrations of GML.

The effect of GML at a range of concentrations and in the presence of a range of pH levels on the growth of Pseudomonas aeruginosa was also determined. P. aeruginosa (strain PAO 1) was inoculated in Todd Hewitt broth at 5.7×106/mL. GML was added to cultures at a range of concentrations from 10 µg/mL to 5000 µg/mL, and the pH was adjusted to 5.0, 6.0, or 7.0. CFU/mL was determined after 24 hours of incubation. The results of the study are shown in FIG. 14. At a pH of 6.0 or 7.0, no concentration of GML was inhibitory for the growth of P. aeruginosa. A pH of 5.0 in the absence of GML was somewhat inhibitory for the growth of P. aeruginosa. However, the addition of GML to the cultures at a pH of 5.0 further inhibited P. aeruginosa growth in a dose-dependent manner (*p<0.001; dashed line indicates starting inoculum size).

The results of the study indicated that GML and a lowered pH synergistically inhibited the growth of pathogenic microorganims.

Example 5: Effect of Non-Aqueous Gel on the Antimicrobial Activity of GML

Non-aqueous gels comprised of propylene glycol (73.55% w/w), polyethylene glycol 400 (25% w/w), and hydroxypropyl cellulose (Gallipot, St Paul, MN; 1.25% w/w), with or without GML, were heated to 65° C. After solubilization of components, the gels were diluted with Todd Hewitt broth to 10%, or 25%. GML alone was also diluted comparably with Todd Hewitt broth to serve as an additional control. S. aureus (strain MN8, a toxic shock syndrome strain) was incubated at 37° C. with shaking (200 RPM) in the various concentrations of non-aqueous gel in the presence of GML at concentrations ranging from 1 µg/mL to 5000 µg/mL, or in the presence of GML alone at the same concentrations. After 24 hours, plate counts (CFU/mL) were determined.

Figure 15:
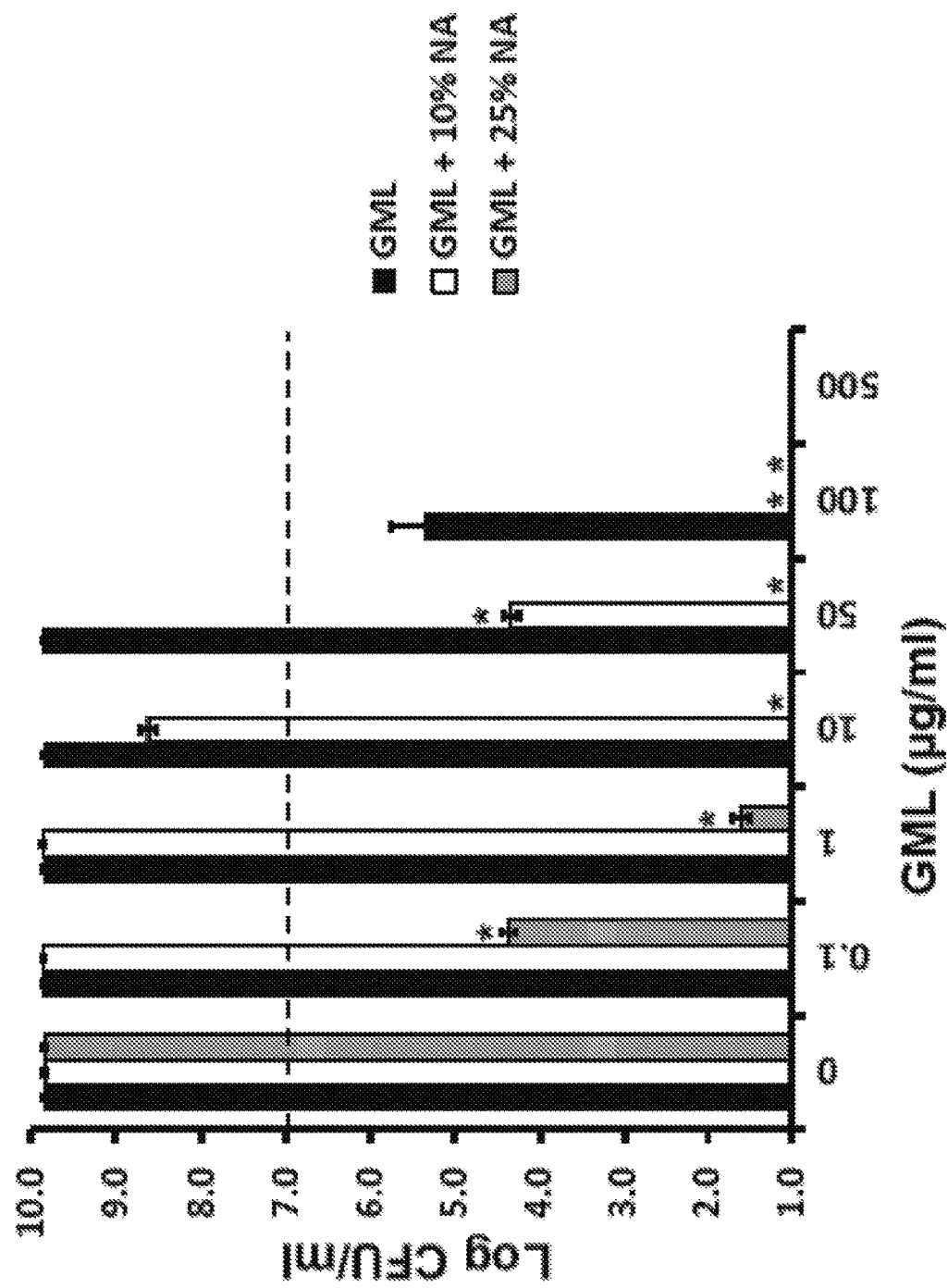
FIG. 15 is a graph showing the effect of the indicated concentrations of GML alone (black), GML in a 10% non-aqueous gel carrier (white) or a 25% non-aqueous gel carrier (grey), on the growth of *S. aureus* (CFU/mL).

FIG. 15 shows the results of the study. GML inhibited the growth of S. aureus at a concentration of 100 µg/mL or above. The 10% and 25%, non-aqueous (NA) gel concentrations, as well as the range of GML concentrations, exhibited dose-dependent effects on the growth of S. aureus. GML in 25% non-aqueous gel had approximately 500-fold greater activity than GML alone, and GML in 10% non-aqueous delivery vehicle had approximately 10-fold greater activity than GML alone (FIG. 15; *p<0.001; dashed line indicates starting inoculum size). Therefore, the combination of the non-aqueous gel and GML had a potent antimicrobial effect.

Example 6: Solubility of Tenofovir in GML Gels

Non-aqueous gels comprised of propylene glycol (73.55% w/w), polyethylene glycol 400 (25% w/w), and hydroxypropyl cellulose (1.25% w/w) at a range of pH from 4.0 to 4.5 were prepared. The anti-HIV drug Tenofovir was added to the gels at a concentration of 10 mg/mL to determine if the drug was soluble in the compositions.

Figure 16:
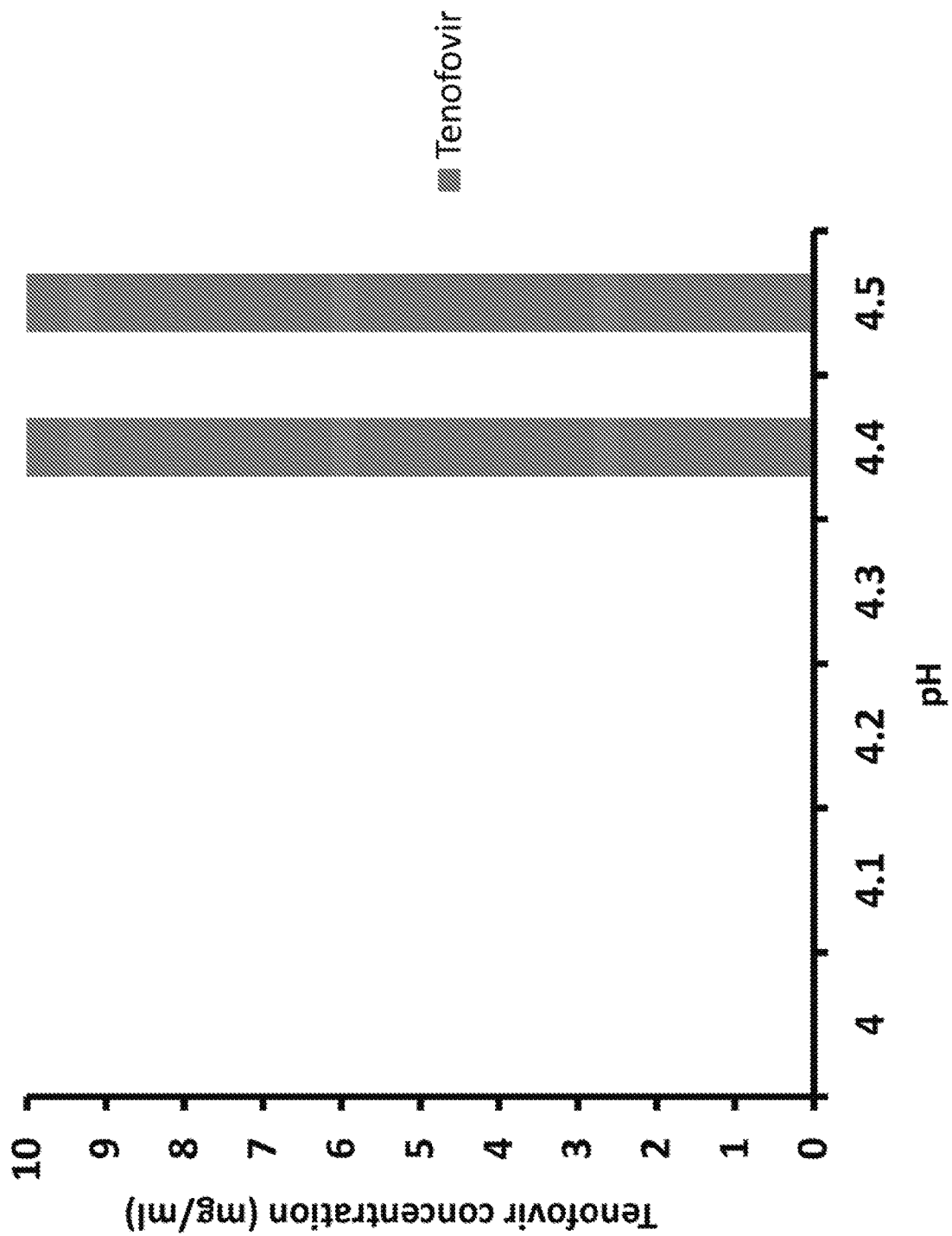
FIG. 16 is a graph depicting the solubility of tenofovir (10 mg/mL) in GML at a pH ranging from 4.0 to 4.5. The absence of a bar indicates that the 10 mg/mL tenofovir was not soluble in the composition, while the presence of a bar indicates that 10 mg/mL tenofovir was soluble in the composition

The results of the study are shown in FIG. 16. Tenofovir (10 mg/mL) was not soluble in the non-aqueous gel at a pH of 4.0-4.3, but was soluble in the non-aqueous gel at a pH of 4.4 or 4.5.

Example 7: Effectiveness of Various Forms of GML

Multiple forms of GML exist, including R or S optical isomers and GML with lauric acid ester linked in the 1/3-position or the 2-position of glycerol. In order to test for potential differences between the optical isomers, the R form of GML, which is commercially available, was compared to a GML racemic mixture of the R and S forms. In order to test for potential differences between GML with lauric acid linked to different glycerol positions, the commercially available purified 2-position lauric acid GML was compared to a mixture of 2-position and 1/3-position lauric acid GML. Antibacterial effects of these forms of GML was assessed on S. pyogenes (strain 594).

Figure 17:
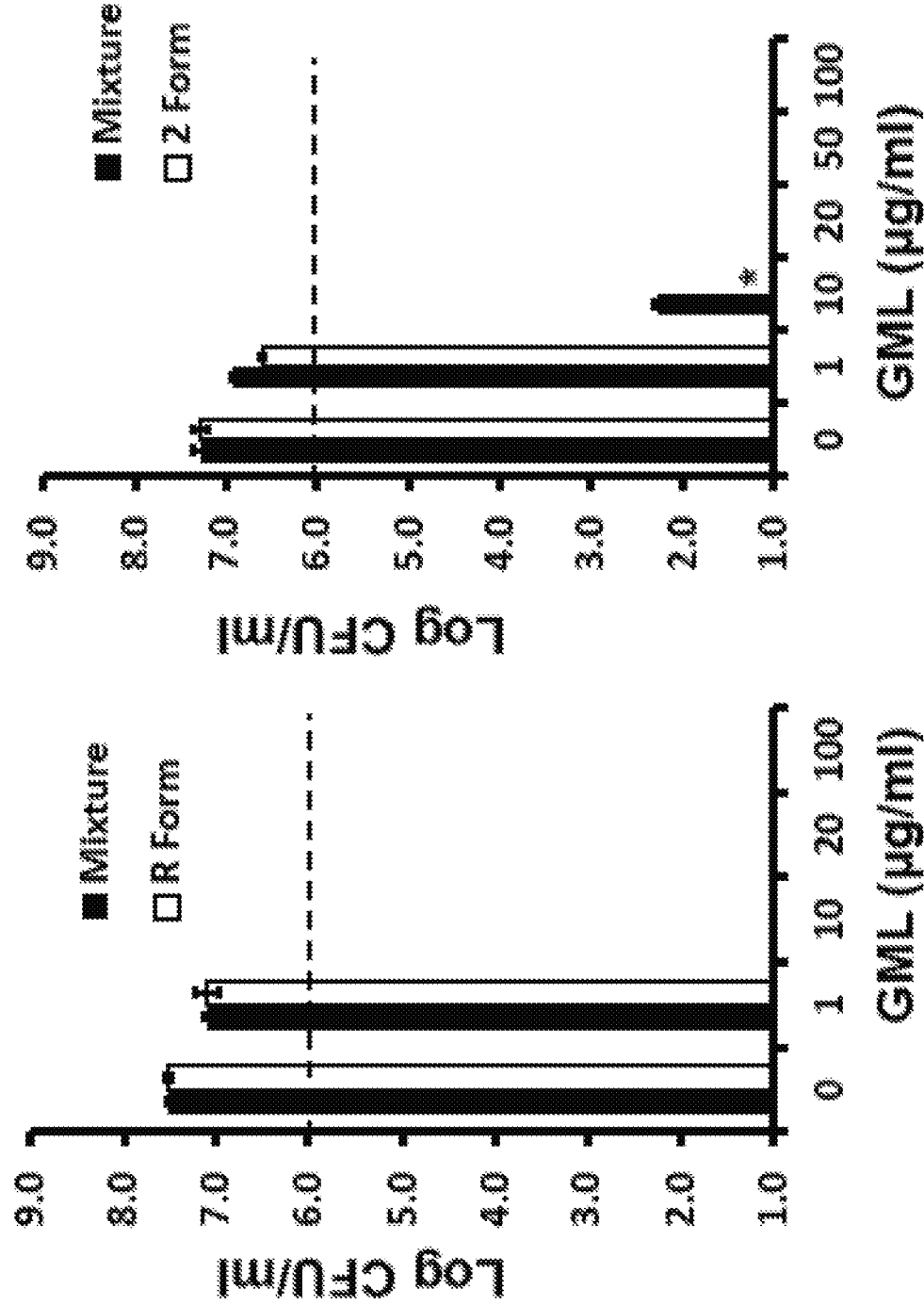
FIG. 17 is a set of graphs showing the bactericidal activity of the indicated forms of GML against *S. pyogenes*.

The results of the study are shown in FIG. 17. The R form GML and the mixture of R and S form GML had the same antibacterial activity (left panel; dashed line indicates starting inoculum size). However, the GML form with lauric acid in the 2-position was 2-fold more active than the mixture of GML forms (right panel; *p<0.001; dashed line indicates starting inoculum size). Therefore, the results indicated that GML activity depended not on chirality, but did to some extent depend on the position of the lauric acid.

Example 8: Antibacterial Activity of GML Versus Lauric Acid

Bactericidal activity, as well as the ability to inhibit exotoxin production, of GML compared to lauric acid (a major cleavage product of GML) was determined. S. aureus, an organism that produces glycerol ester hydrolase (GEH), and S. pyogenes, which does not produce GEH, were tested.

Figure 18:
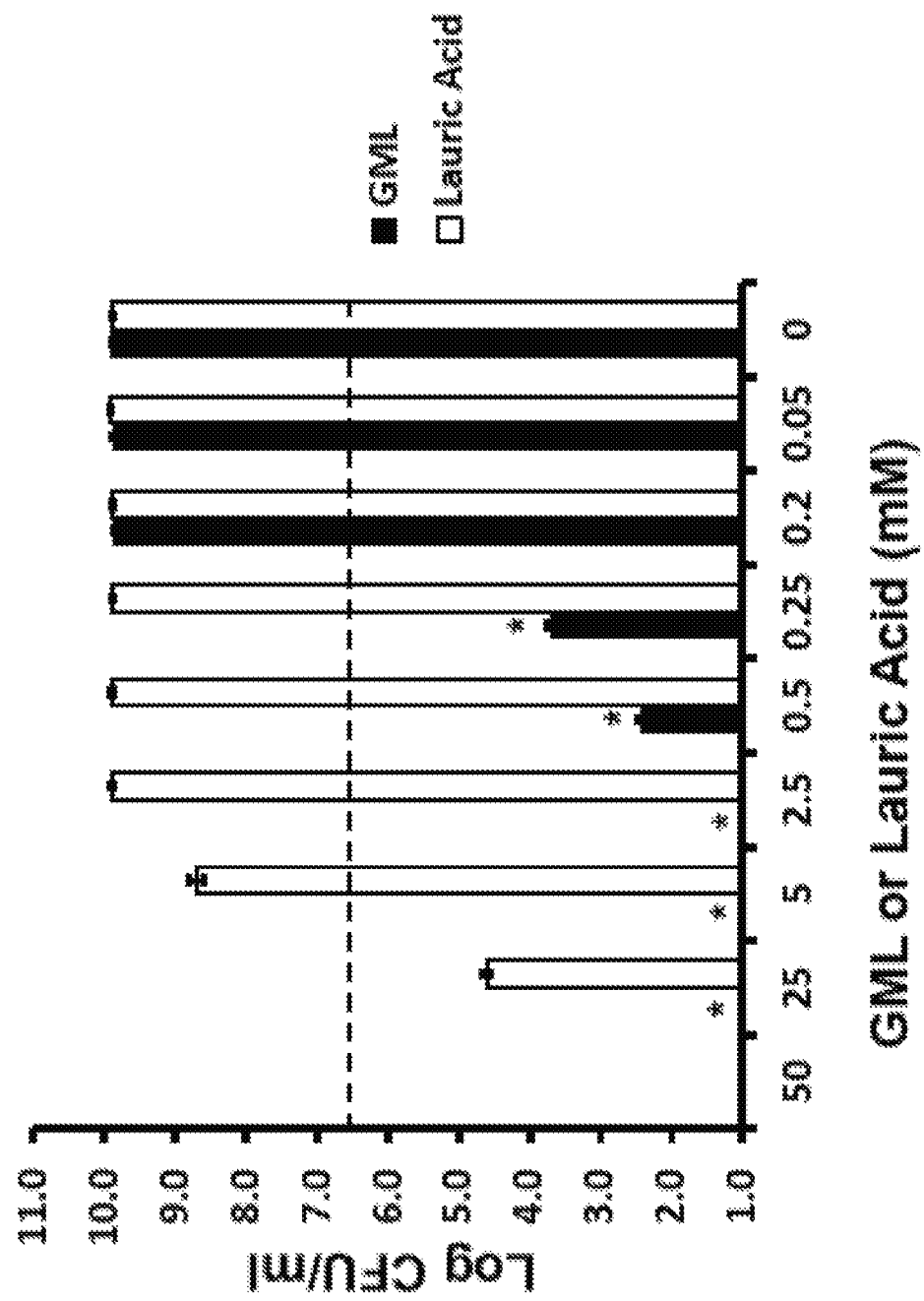
FIG. 18 is a graph showing the bactericidal activity (CFU/mL) of GML compared to lauric acid, in the presence of *S. pyogenes*.
Figure 19:
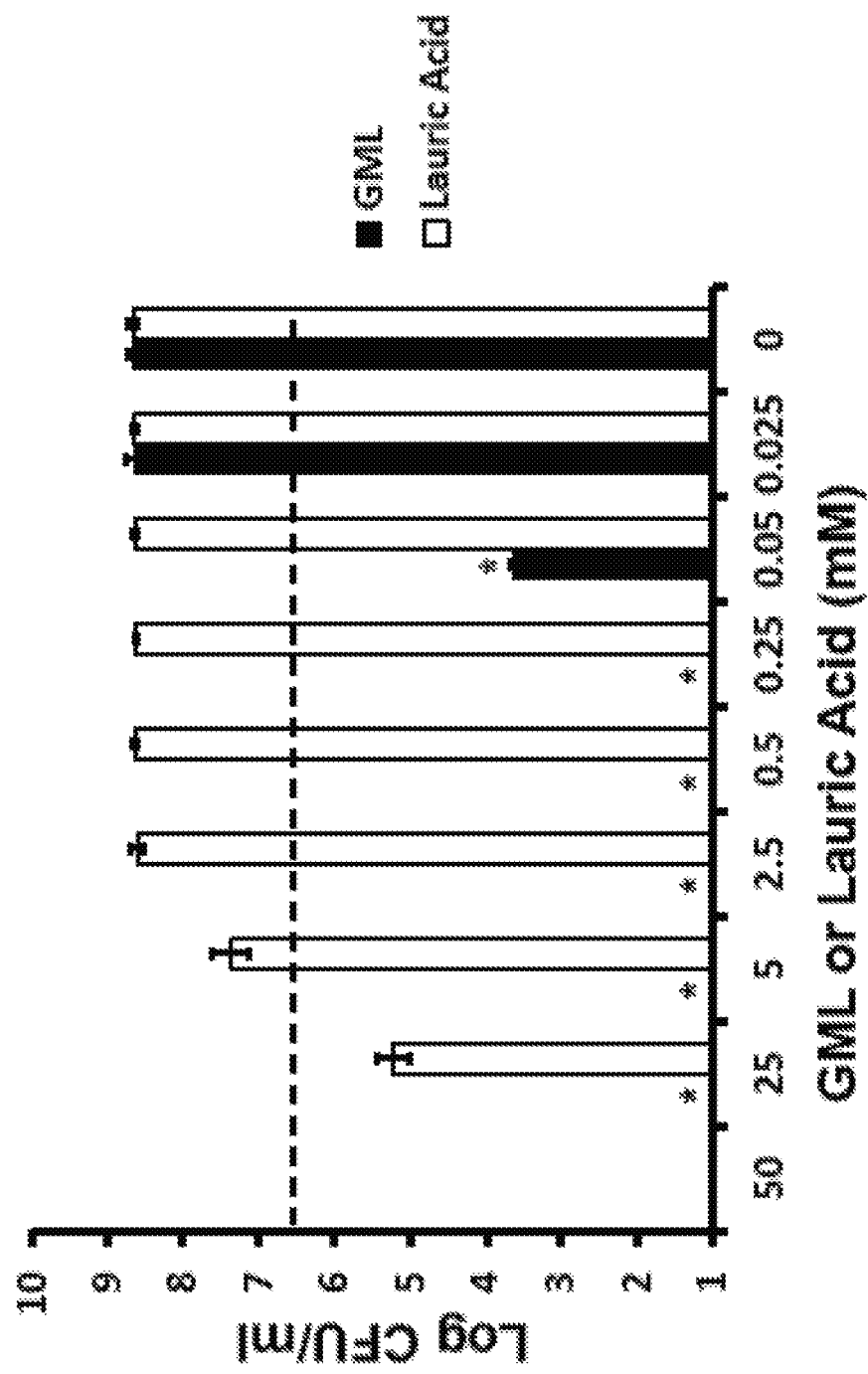
FIG. 19 is a graph showing the bactericidal activity (CFU/mL) of GML compared to lauric acid, in the presence of *S. aureus*.

The results of the study with regard to the bactericidal activity of GML and lauric acid are shown in FIGS. 18 and 19. GML and lauric acid were incubated at the indicated concentrations with approximately 5×106 CFU/mL S. aureus MN8 (FIG. 18) or S. pyogenes (FIG. 19) for 24 hours at 37° C., in triplicate. For S. aureus, plates were incubated with shaking (200 RPM). For S. pyogenes, plates were incubated stationary in the presence of 7% CO2. Plate counts were used to determine CFU/mL. Bactericidal activity was defined as the minimum concentration of GML or lauric acid required to reduce CPUs by at least 3 logs. GML was bactericidal for S. aureus at 200-fold lower concentrations than lauric acid (FIG. 18; *p<0.001; dashed line indicates starting inoculum size). GML was bactericidal for S. pyogenes at 500-fold lower concentrations than lauric acid (FIG. 19; *p<0.001; dashed line indicates starting inoculum size). In addition, in comparing the bactericidal activity of GML against the two organisms, GML was 5-fold more bactericidal for S. pyogenes than for S. aureus.

To determine the relative capacity of GML and lauric acid to inhibit superantigen production, S. aureus MN8 and S. pyogenes were cultured for 8 hours in the presence of GML or lauric acid. TSST-1 production by S. aureus MN8 and streptococcal pyrogenic exotoxin A (SPE A) production by S. pyogenes were quantified by Western immunoblot analysis.

Figure 20:
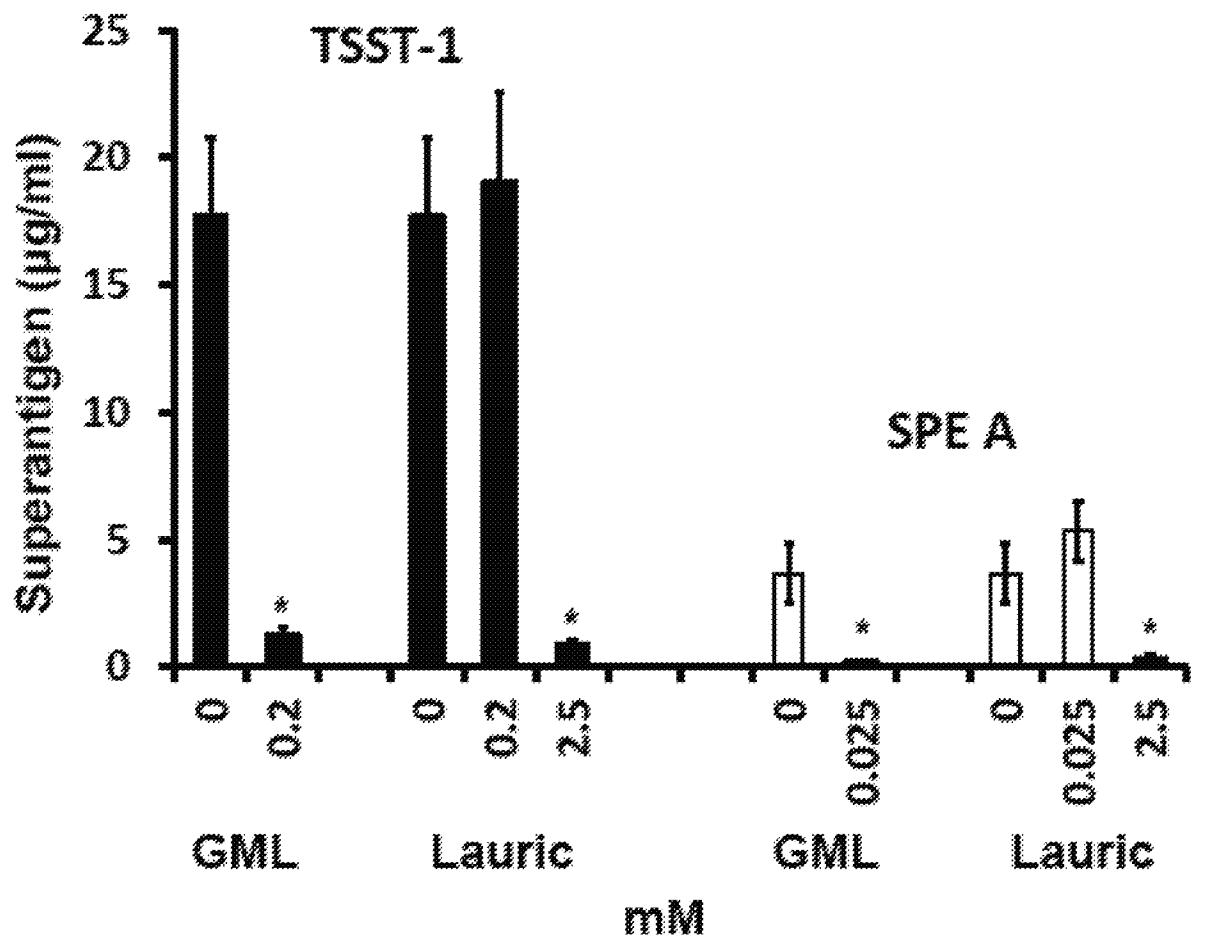

The results of the study with regard to superantigen production are shown in FIG. 20. Both GML and lauric acid significantly inhibited exotoxin production by S. aureus MN8 and S. pyogenes at concentrations that were not growth inhibitory. However, the concentration of GML required for inhibition of exotoxin production was lower for both organisms, compared to the concentration of lauric acid required to inhibit exotoxin production. GML inhibited production of S. aureus TSST-1 at a concentration of 0.2 µg/mL, and inhibited production of S. pyogenes SPE A at a concentration of 0.025 µg/mL, while lauric acid inhibited production of both TSST-1 and SPE A at a concentration of 2.5 µg/mL. (*p<0.01).

To further assess the differences between S. aureus and S. pyogenes with regard to GML activity, GML was pre-treated by incubating overnight at a concentration of 1000 µg/0.4 mL Todd Hewitt broth with 0.1 mL of stationary phase sterile culture fluid from S. aureus MN8 or S. pyogenes.

Figure 21:
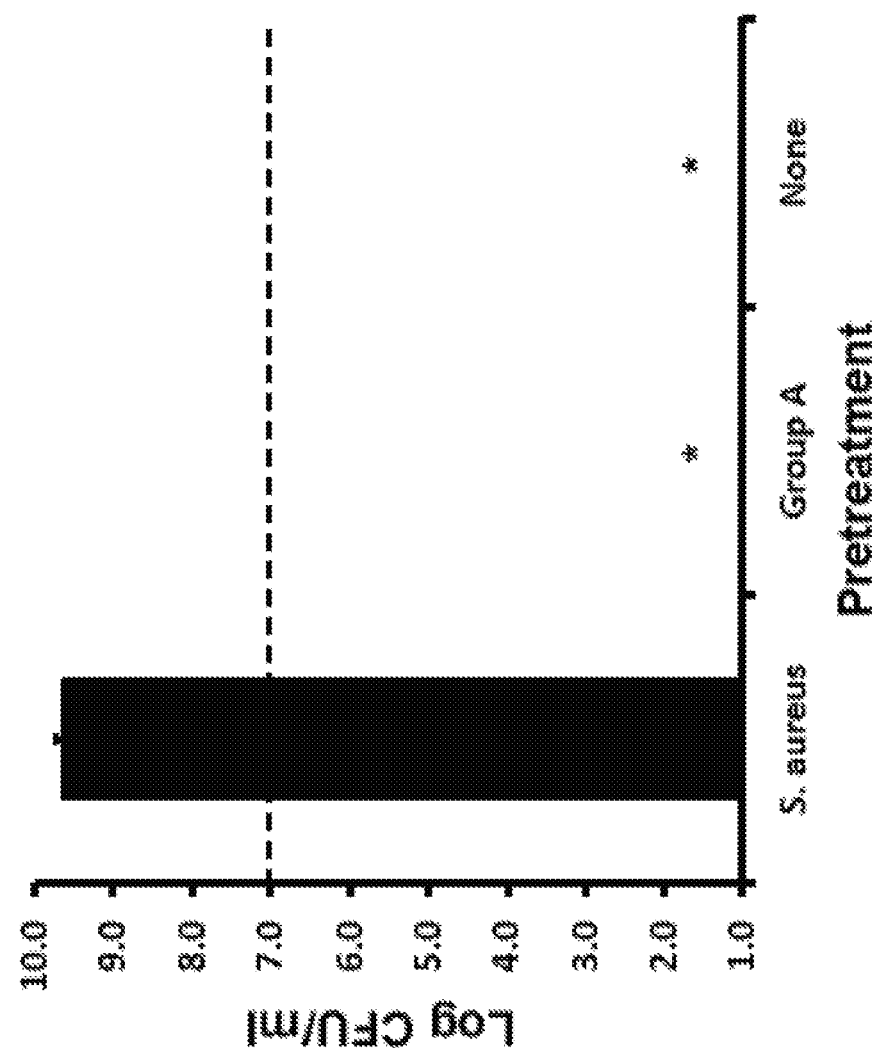
FIG. 21 is a graph showing the bactericidal activity of GML after pre-treatment with S. aureus or S. pyogenes.

The results of the study are shown in FIG. 21. Pre-incubation with S. aureus eliminated the antibacterial activity of GML against S. aureus MN8 as measured in the 24 hour assay described above. However, pre-incubation with S. pyogenes did not affect GML's antibacterial activity. (*p<0.001; dashed line indicates starting inoculum size.) These results suggested that an esterase produced by S. aureus, such as GEH, inhibited GML activity.

Example 9: Development of Resistance to GML in S. Aureus

To determine if S. aureus developed resistance to GML, S. aureus cultures were treated with sub-optimal concentrations of GML (50 µg/mL) for one year. Each week, S. aureus strain MN8 was transferred to Todd Hewitt agar plates containing 50 µg/mL GML and cultured for 48 hours. This sub-optimal GML concentration allows S. aureus to grow for 48 hours. Organisms that grew were passed weekly onto new plates containing 50 µg/mL GML, or were transferred to plates containing 100 µg/mL GML, a concentration at which S. aureus cannot normally grow, for 24 hours. In addition, 50 g/mL GML plates were placed at 4° C. weekly to allow GML to crystalize. Plates were analyzed for non-crystalizing zones around individual S. aureus colonies, which is indicative of GEH cleavage of GML.

Despite the fact that S. aureus exhibits rapid development of resistance to many antibiotics, no S. aureus developed that was able to grow on 100 µg/mL GML plates. Therefore, S. aureus did not develop resistance to GML over the period of one year. In addition, no mutants that had upregulated GEH production during the year of passage were identified (data not shown).

Example 10: Decolonization Studies

A study was undertaken to assess the ability of GML (5% w/v), formulated in a non-aqueous gel, to decolonize the respiratory tract in humans, and to decolonize contaminated surgical incision sites in experimental rabbits.

Three human subjects underwent swabs of the anterior nares in order to assess whether GML was capable of decolonizing the respiratory tract. Swabs were dipped in phosphate-buffered saline (PBS), which has previously been shown to result in the uptake of 0.1 ml of PBS, and then used to swab anterior nares of each subject. The swabs were rotated around each nare up to the nasal bone 3 times. Colony-forming units of microbes from swabs were determined by plate counts on blood agar and mannitol salt agar. The anterior nares were then treated in the same way with swabs that had been dipped one time in GML gel. The anterior nares of each participant were swabbed at designated time periods for up to 24 hours, and swabs were cultured for S. aureus and coagulase-negative staphylococci.

Figure 22:
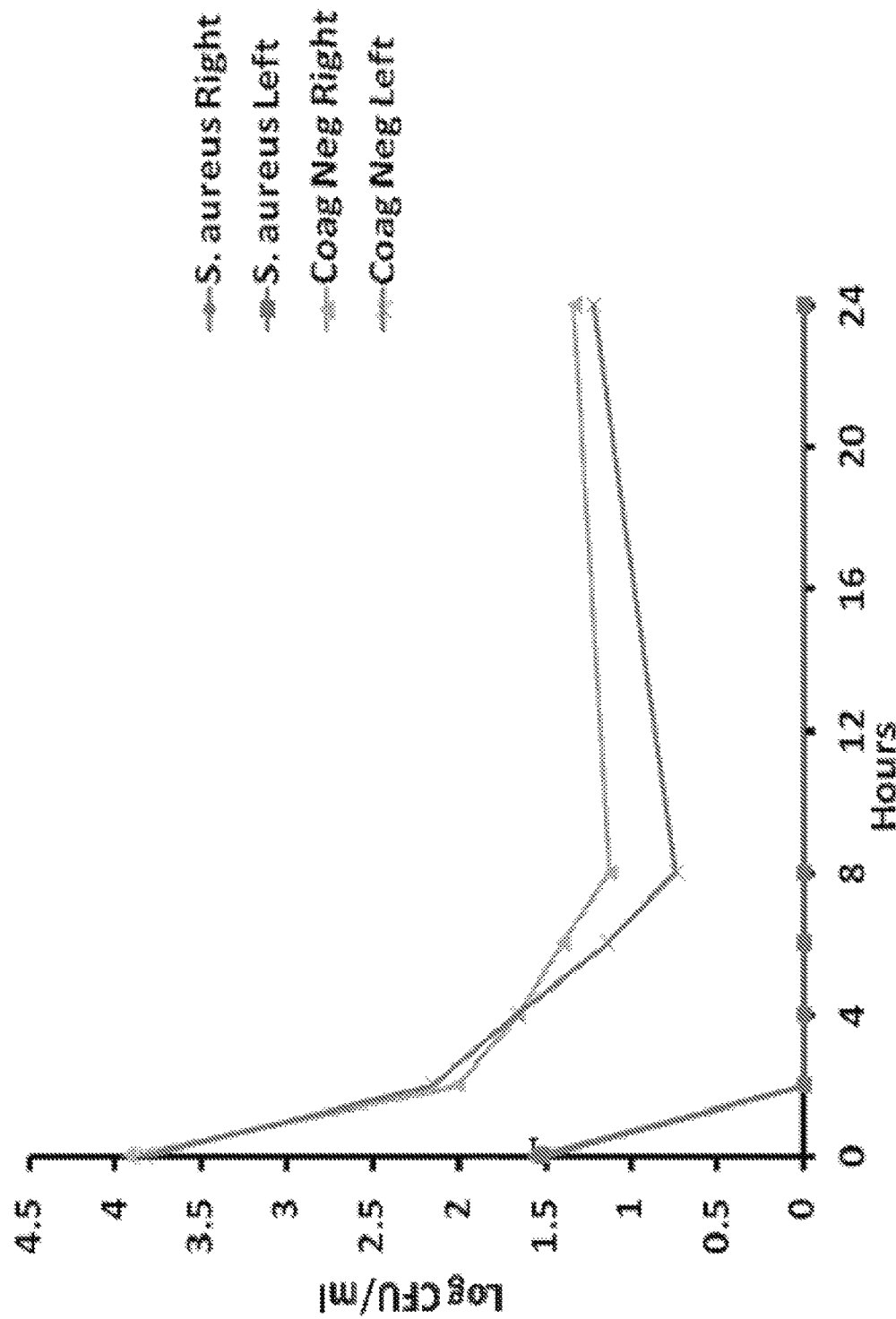
FIG. 22 is a graph showing the staphylococcal counts (CFU/mL) in anterior nares of three human subjects treated with 5% GML in a non-aqueous gel.

The data obtained from this study are shown in FIG. 22. Data were log transformed prior to performing statistics due to the high variability in CPUs present in the three subjects. The right and left anterior nares of the three subjects contained an average log CFU/mL S. aureus of 1.6 or 1.5, respectively, prior to GML treatment. GML treatment significantly ($p<0.05$ by Student's t test analysis) reduced S. aureus counts in both nares to 0 CFU/mL at all tested time-points after treatment, including the 24 hour time-point. The right and left anterior nares of the three subjects contained an average log CFU/mL of coagulase-negative staphylococci of 3.9 and 3.8, respectively, prior to GML treatment. GML treatment significantly ($p<0.05$) reduced coagulase-negative staphylococcal counts in both nares at tested time-points of 4 hours or more after treatment, including the 24 hour time-point.

For one subject, the persistence of reduced CPUs of both S. aureus and coagulase-negative staphylococci were tested over 3 days. S. aureus counts remained at 0 for the entire 3 day test period. The CPUs of coagulase-negative staphylococci also remained low for the entire time period (initially there were 560 and 880 CFU/mL in the right and left nares, respectively; after 3 days, 8 and 0 CFU/mL of coagulase-negative staphylococci were detected in the right and left nares, respectively; data not shown).

Studies were next performed to assess whether 5% GML gel could decolonize teeth of oral aerobic bacteria. Human volunteers were swabbed with a PBS-saturated swab across the teeth and gum lines on the left side of the mouth and tested for CFU/mL of total bacteria subsequently grown on blood agar plates. The same individuals were then swabbed with GML gel by swabbing the gel across the teeth and gum lines on the right side of the mouth. Enough gel was used to coat the entire surface area of the teeth and gum lines. Thirty minutes after treatment, the participants were swabbed with PBS-saturated swabs on the right side and total CFU/mL were determined.

To ensure that the data obtained did not differ simply due to removal of bacteria by the initial swab, different sides of the teeth and gum lines for the pre- and post-treatment swabs were used. Bacterial counts on both sides of the teeth and gum lines were presumed to be approximately equal, and a pre-test swab confirmed that this was the case.

Figure 23:
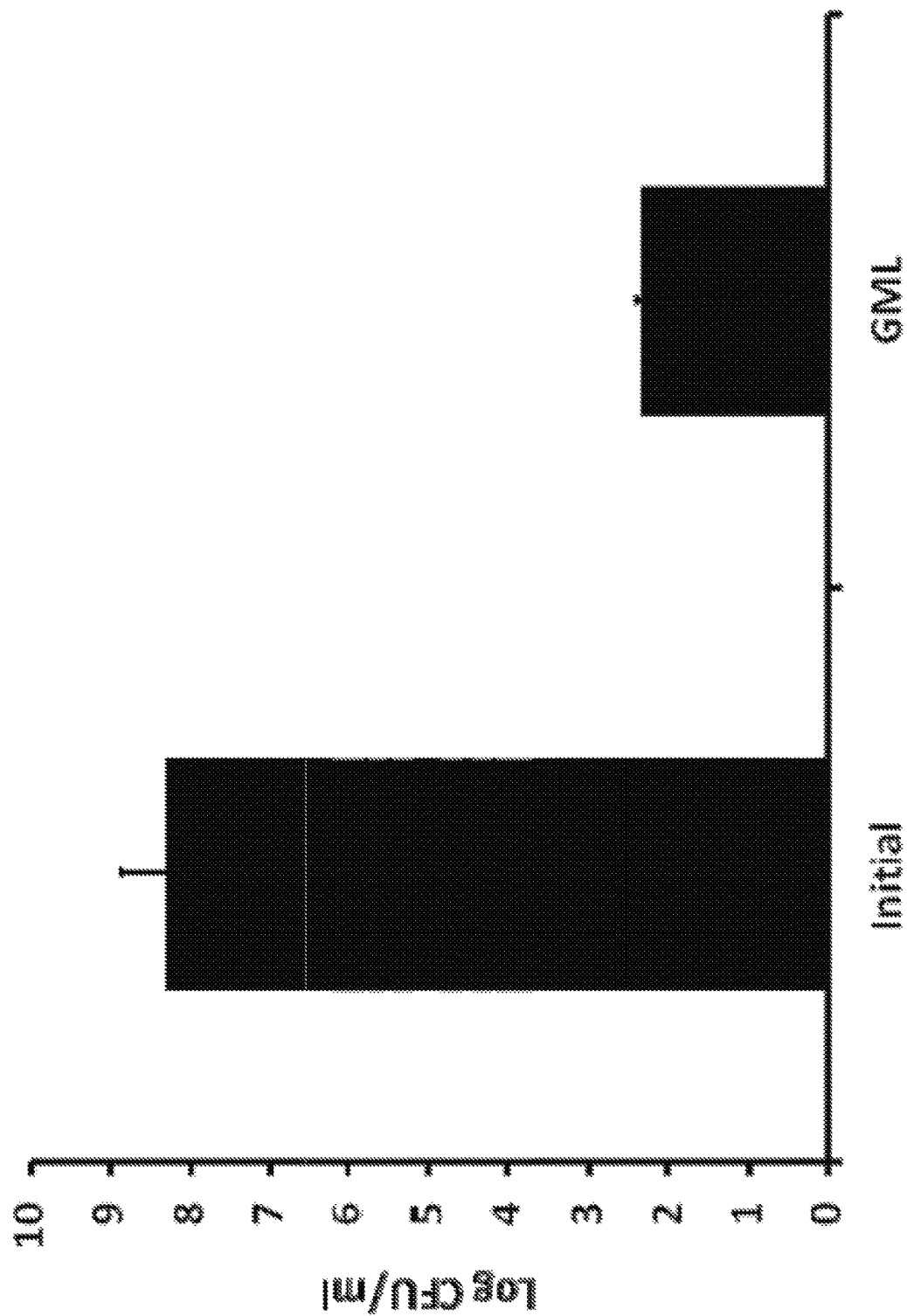
FIG. 23 is a graph showing the ability of 5% GML in a non-aqueous gel to reduce aerobic bacteria on human teeth and gum lines (CFU/mL).

The results of the study are shown in FIG. 23. Data were log transformed to account for high variability in CFU/mL among subjects. There was a >5 log reduction in CPUs between the pretreatment swabs and the post-treatment swabs, indicating the GML killed the bacteria adhering to the teeth, which were primarily oral streptococci. Since GML was effective in reducing counts, the data also suggested that GML gel was effective in removing and/or killing bacteria in biofilms, which would be expected to be present on teeth. The data were highly significantly different as tested by Student's t test analysis ($p<0.001$).

In a final study, S. aureus strain MN8 ($I \times 1010$ CFU) was used to coat surgical incision sites of three rabbits per group. The surgical incision sites were 4 cm subcutaneous incisions that had been closed with 4 silk sutures (Ethicon, Cornelia, GA). After closing, GML 5% w/v non-aqueous gel was swabbed onto the incision sites of three animals, and PBS was swabbed onto the incision sites of control animals. Enough GML gel was swabbed to provide a uniform coating of the surface. After 24 hours, the rabbits were examined for inflammation (as determined by redness in the incision sites) and total CFU/mL that could be obtained by swabbing the incision sites with PBS-saturated swabs.

Figure 24:
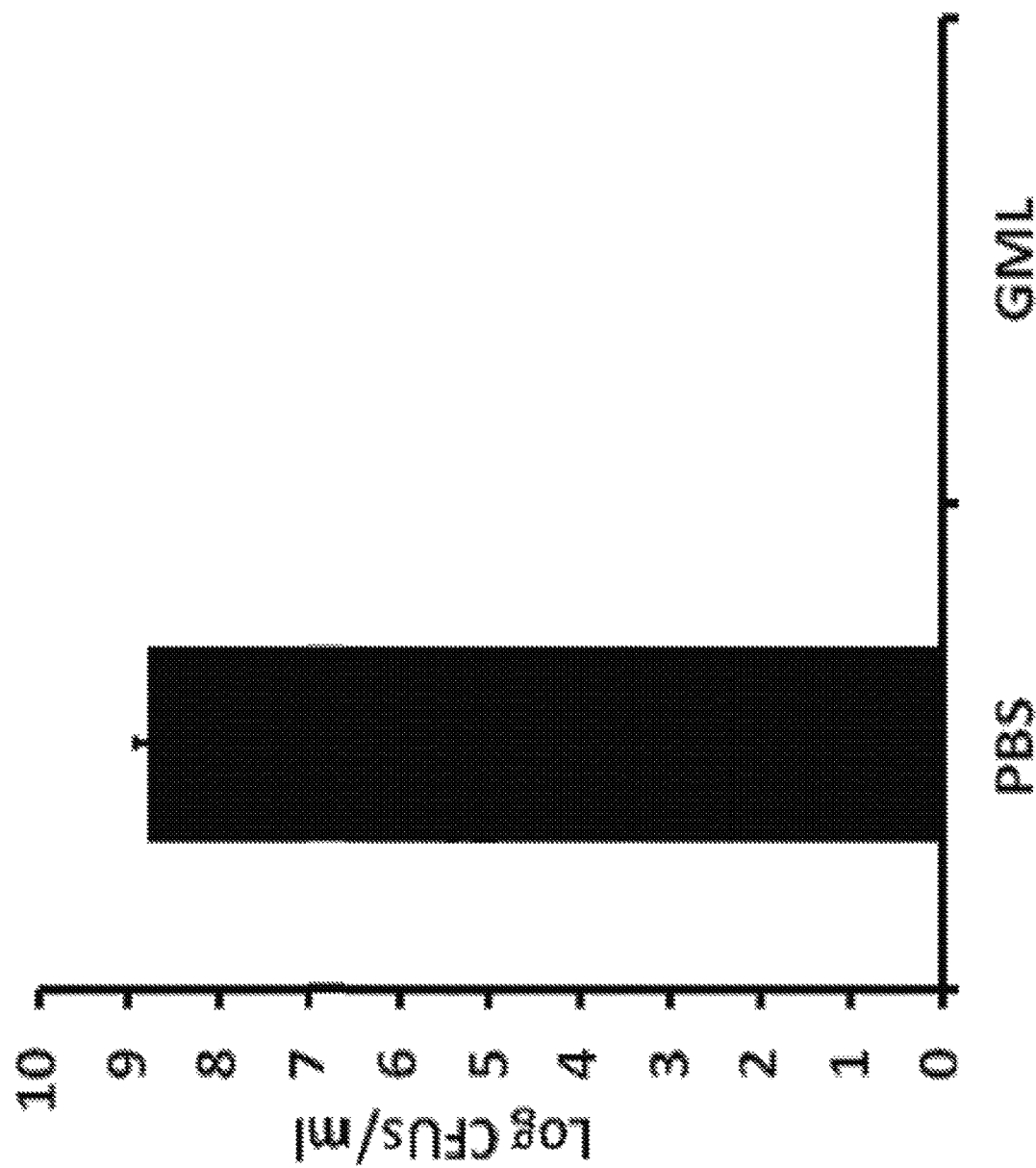
FIG. 24 is a graph showing the presence of S. aureus on surgical incision sites of rabbits 24 hours after swabbing with S. aureus MN8 and either PBS or 5% GML

The results of the study are shown in FIGS. 24 and 25. Rabbits that were swabbed with PBS had an average of 8.8 log CFU/mL of S. aureus at the 24 hour time-point (FIG. 24) and obvious inflammation at the surgical site (FIG. 25). In contrast, in rabbits that had been treated with GML, no CPUs were detectable at the 24 hour time-point (FIG. 24; $p<<0.001$ by Student's t test analysis of log transformed data) and less inflammation at the surgical site (FIG. 25).

Collectively, the data presented in this study showed that a 5% GML non-aqueous gel could be used effectively to reduce colonization of the nasal and oral cavities of humans and rabbit surgical incision sites by potential pathogens.

Example 11: Clinical Efficacy of GML in Vaginal Infection

The following prophetic example provides a proposed clinical study wherein the relative effectiveness of a composition comprising GML, a vegetable oil, and a pharmaceutically acceptable topical carrier will be determined for the treatment of BV or VVC. This prophetic example is intended to illustrate the principles of the present invention.

The study design is a single-center, double-blind study of 60 subjects, 20 subjects per arm. Subjects will be stratified based on type of vaginal infection (BV, VVC, or both) and age.

Study subjects will be females aged 18-50 with BV or VVC (as determined by gynecological exam conducted during the screening visit) who have signed Informed Consent. Pregnant women, menstruating women, and women who have had a systemic infection or have used a vaginal anti-microbial, anti-inflammatory, or immunosuppressant medication within the previous 4 weeks will be excluded.

Study endpoints and treatment evaluation: A vaginal swab will be collected at the baseline visit. Subjects will vaginally self-administer one of the following every 12 hours for two days, for a total of 4 doses: 0% (vehicle control), 0.5%, or 5% GML in olive oil. Vaginal swabs will be collected 12 and 48 hours after the final dose of study drug or vehicle control. Colony Forming Units (CFU) will be determined for Lactobacillus, G. vaginalis, and Candida on baseline and treatment follow-up vaginal swabs. Subjects will be followed for a period of 3 months and all adverse events including clinical findings and opportunistic infections will be recorded.

The results of the proposed study will be employed in the development of a clinical protocol for the treatment of BV or VVC.

Example 12: Clinical Use of GML in Urinary Tract Infection

The following prophetic example is intended to illustrate circumstances wherein the formulations herein disclosed are indicated.

A subject at risk of urinary tract infections (e.g., for example, a woman or an elderly individual) may apply a composition comprising 50 µg/mL GML to a sponge, and then apply the sponge to the area of the external urethral opening or orifice. The composition may be applied once per day to prevent urinary tract infections. The composition may additionally comprise an accelerant such as EDTA and/or a non-aqueous gel.

Example 13. Clinical Use of GML in Cellulitis

The following prophetic example is intended to illustrate circumstances wherein the formulations herein disclosed are indicated.

A subject that has been diagnosed with cellulitis may topically self-administer a composition comprising 5 pig/mL GML and 25% non-aqueous gel in a pharmaceutically acceptable topical carrier to the site of the skin infection, twice per day until the infection resolves. If medically indicated, the patient may also be administered an antibacterial agent.

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A method of treating or preventing a gram-positive bacterial skin infection, a gram-positive bacterial infection of a wound, or a gram-positive bacterial infection of surgical incision cite in a subject in need thereof, the method comprising the step of topically administering an effective amount of a composition comprising GML and a non-aqueous gel comprised of a combination of propylene glycol, polyethylene glycol, and cellulose derivative and the non-aqueous gel having a pH from about 4.0 to about 4.5, wherein the non-aqueous gel is at a concentration of about 10% to about 25% of the composition, to treat or prevent the gram-positive bacterial skin infection, the gram-positive bacterial infection of a wound, or the gram-positive bacterial infection of surgical incision cite in the subject, wherein GML is present at a concentration of about 10 µg/mL to about 100 mg/mL; and wherein the GML is the isomer of GML with lauric acid in the 2-position of glycerol.

2. The method of 1, wherein the non-aqueous composition further comprises a pharmaceutically acceptable topical carrier.

3. The method of 1, wherein the non-aqueous composition further comprises an accelerant selected from an organic acid, a chelator, an antibiotic agent, an anti-fungal agent, an anti-viral agent, or a combination thereof.

4. The method of 1, wherein GML comprises about 0.001% (w/v) to about 10% (w/v) of the composition.

5. The method of 1, further comprising administering a second active agent selected from an antibiotic, an anti-fungal agent, or an anti-viral agent.

6. The method of claim 1, wherein the gram-positive bacterial infection is a *Staphylococcus* infection.

7. The method of claim 1 wherein the gram-positive bacterial infection is methicillin-resistant *Staphylococcus aureus*.

8. The method of 1, wherein the gram-positive bacterial infection is a *Streptococcus* infection.

9. The method of 1, wherein the subject is a human.

10. The method of 1, the method further comprising using a sponge, wipe, or swab to topically apply the non-aqueous composition.

* * * * *